(12) United States Patent
Simonyan et al.

(10) Patent No.: US 11,000,828 B2
(45) Date of Patent: May 11, 2021

(54) METHOD OF MAKING SURFACE-COATED WATER-ABSORBING POLYMER PARTICLES IN A MICROFLUIDIC DEVICE

(71) Applicant: The Procter & Gamble Company, Cincinnati, OH (US)

(72) Inventors: Arsen Simonyan, Schwalbach (DE); Juliane Kamphus, Schwalbach (DE); Sebastian Seiffert, Mainz (DE); Axel Kai Tobias Habicht, Mainz (DE)

(73) Assignee: The Procter & Gamble Company, Cincinnati, OH (US)

( * ) Notice: Subject to any disclaimer, the term of this patent is extended or adjusted under 35 U.S.C. 154(b) by 95 days.

(21) Appl. No.: 15/954,640

(22) Filed: Apr. 17, 2018

(65) Prior Publication Data

US 2018/0304233 A1    Oct. 25, 2018

(30) Foreign Application Priority Data

Apr. 19, 2017  (EP) ........................... 17167083
Mar. 20, 2018  (WO) .................. US2018/023275

(51) Int. Cl.
*A61L 15/24*        (2006.01)
*A61L 15/60*        (2006.01)
(Continued)

(52) U.S. Cl.
CPC ............. *B01J 20/267* (2013.01); *A61L 15/24* (2013.01); *A61L 15/60* (2013.01); *B01J 20/28004* (2013.01); *B01J 20/28016* (2013.01); *B01J 20/3208* (2013.01); *B01J 20/3231* (2013.01); *B01J 20/3234* (2013.01); *B01J 20/3282* (2013.01); *B01J 20/3289* (2013.01); *B01J 20/3293* (2013.01); *B01J 20/3295* (2013.01); *C08J 3/126* (2013.01); *C08J 3/245* (2013.01);
(Continued)

(58) Field of Classification Search
CPC . A61L 15/24; A61L 15/60; B01J 20/26; B01J 20/28; B01J 20/32; C08J 3/12; C08J 3/24
See application file for complete search history.

(56) References Cited

U.S. PATENT DOCUMENTS 4,666,983 A    5/1987  Tsubakimoto et al.
5,331,059 A    7/1994  Engelhardt et al.
(Continued)

FOREIGN PATENT DOCUMENTS

DE    10204937 A1    8/2003
EP      083022       7/1983
(Continued)

*Primary Examiner* — Alexander M Weddle
(74) *Attorney, Agent, or Firm* — Brian M. Bolam

(57) ABSTRACT

A method for making surface-coated water-absorbing polymer particles in a microfluidic device is provided. The microfluidic device includes a first microfluidic channel conveying precursor water-absorbing polymer particles, a second microfluidic channel conveying a first coating solution, a third microfluidic channel conveying water-absorbing polymer particles coated with the first coating solution, a fourth microfluidic channel conveying a first non aqueous liquid. An absorbent article includes the surface-coated water-absorbing polymer particles obtained via the method herein is also provided.

12 Claims, 11 Drawing Sheets

(51) Int. Cl.
  *C08J 3/24* (2006.01)
  *B01J 20/26* (2006.01)
  *C08J 3/12* (2006.01)
  *B01J 20/28* (2006.01)
  *B01J 20/32* (2006.01)

(52) U.S. Cl.
  CPC ........ *B01J 2220/68* (2013.01); *C08J 2333/02* (2013.01)

(56) References Cited

U.S. PATENT DOCUMENTS

| | | | |
|---|---|---|---|
| 5,409,771 | A | 4/1995 | Dahmen et al. |
| 5,700,254 | A | 12/1997 | McDowall et al. |
| 5,731,365 | A | 3/1998 | Engelhardt et al. |
| 5,837,789 | A | 11/1998 | Stockhausen et al. |
| 6,143,821 | A | 11/2000 | Houben |
| 6,472,478 | B1 | 10/2002 | Funk et al. |
| 6,503,979 | B1 | 1/2003 | Funk et al. |
| 6,559,239 | B1 | 5/2003 | Riegel et al. |
| 6,657,015 | B1 | 12/2003 | Riegel et al. |
| 6,710,141 | B1 | 3/2004 | Heide et al. |
| 6,911,499 | B1 | 6/2005 | Brehm et al. |
| 7,199,211 | B2 | 4/2007 | Popp et al. |
| 7,250,481 | B2 | 7/2007 | Jaworek et al. |
| 7,652,111 | B2 | 1/2010 | Hermeling et al. |
| 7,687,596 | B2 | 3/2010 | Hermeling et al. |
| 7,754,822 | B2 | 7/2010 | Daniel et al. |
| 7,772,420 | B2 | 8/2010 | Hermeling et al. |
| 2003/0105190 | A1 | 6/2003 | Diehl et al. |
| 2005/0031868 | A1 | 2/2005 | Fossum et al. |
| 2005/0043696 | A1* | 2/2005 | Schmidt ................. A61L 15/60 604/372 |
| 2005/0165208 | A1 | 7/2005 | Popp et al. |
| 2008/0242817 | A1 | 10/2008 | Ducker et al. |
| 2011/0095227 | A1* | 4/2011 | Herth .................... C08F 220/60 252/194 |
| 2014/0227684 | A1 | 8/2014 | Hindson et al. |
| 2014/0378322 | A1 | 12/2014 | Hindson et al. |
| 2015/0292888 | A1 | 10/2015 | Haglund et al. |
| 2017/0259267 | A1* | 9/2017 | Kim .................... B01L 3/50273 |

FOREIGN PATENT DOCUMENTS

| | | | |
|---|---|---|---|
| EP | 149880 | A2 | 7/1985 |
| EP | 530438 | A1 | 3/1993 |
| EP | 547847 | | 6/1993 |
| EP | 559476 | A1 | 9/1993 |
| EP | 632068 | A1 | 1/1995 |
| EP | 686650 | A1 | 12/1995 |
| EP | 937736 | A2 | 8/1999 |
| EP | 955086 | A2 | 11/1999 |
| EP | 1199327 | A2 | 4/2002 |
| EP | 2277557 | A1 * | 1/2011 ............ A61L 15/60 |
| EP | 2277557 | A1 | 1/2011 |
| WO | WO9015830 | A1 | 12/1990 |
| WO | WO93021237 | A1 | 10/1993 |
| WO | WO95010996 | A1 | 4/1995 |
| WO | WO200059430 | A1 | 10/2000 |
| WO | WO01045758 | A1 | 6/2001 |
| WO | WO02032962 | A2 | 4/2002 |
| WO | WO02067809 | A2 | 9/2002 |
| WO | WO03031482 | A1 | 4/2003 |
| WO | WO2006082242 | A2 | 8/2006 |
| WO | WO2006097389 | A2 | 9/2006 |
| WO | WO2012170778 | | 12/2012 |
| WO | WO-2014057424 | A2 * | 4/2014 |
| WO | WO2014057424 | A2 | 4/2014 |

\* cited by examiner

METHOD OF MAKING SURFACE-COATED WATER-ABSORBING POLYMER PARTICLES IN A MICROFLUIDIC DEVICE

FIELD OF THE INVENTION

The invention relates to a method of making surface-coated water-absorbing polymer particles in a microfluidic device and to an absorbent article comprising the surface-coated water-absorbing polymer particles obtained via the method herein. The invention also relates to surface-coated water-absorbing polymer particles having a specific caliper ratio and to an absorbent article comprising this surface-coated water-absorbing polymer particles. The absorbent articles include, but are not limited to baby diapers, training pants, feminine hygiene sanitary pads and adult incontinence products.

BACKGROUND OF THE INVENTION

An important component of a disposable absorbent article such as a diaper is an absorbent core including water-absorbing polymer particles. This water-absorbing polymer particle ensures that large amounts of bodily fluids, e.g. urine, can be absorbed by the article during its use and locked away, thus providing low rewet and good skin dryness. Especially useful water-absorbing polymer particles are often made by initially polymerizing unsaturated carboxylic acids or derivatives thereof, such as acrylic acid, alkali metal (e.g. sodium and/or potassium) or ammonium salts of acrylic acid, alkyl acrylates, and the like.

These water-absorbing polymer particles need to have adequately high absorption capacity, as well as adequately high gel strength. Absorption capacity needs to be sufficiently high to enable the absorbent polymer to absorb significant amounts of the aqueous body fluids encountered during use of the absorbent article. Gel strength relates to the tendency of the swollen water-absorbing polymer particles (i.e. gel) to resist deformation under an applied stress in the disposable absorbent article. The gel strength needs to be high enough in the absorbent article to avoid excessive deformation of the water-absorbing polymer particles and thereby avoiding blocking of the capillary void spaces between the water-absorbing polymer particles to an unacceptable degree, which would cause so-called gel blocking. This gel-blocking considerably reduces the rate of fluid uptake and/or the fluid distribution: i.e. once gel-blocking occurs, it can substantially impede the distribution of fluids to relatively drier zones or regions in the absorbent article. Leakage from the absorbent article can take place well before the water-absorbing polymeric materials are fully saturated or before the fluid can diffuse or wick past the "blocking" particles into the rest of the absorbent article. Thus, it is important that the water-absorbing polymeric materials (when incorporated in an absorbent core) maintain a high wet-porosity and have a high resistance against deformation thus yielding high permeability for fluid transport through the swollen gel bed.

Water-absorbing polymeric materials with relatively high permeability can be made by increasing the level of internal cross-linking or surface cross-linking, which increases the resistance of the swollen gel against deformation by an external pressure (such as the pressure caused by the wearer), but these techniques typically also reduce the absorbent capacity of the gel.

However, the inventors have found that often the surface-coated water-absorbing polymer particles are constrained by the surface-coating and cannot absorb and swell sufficiently, and/or the surface-coating is not strong enough around the water-absorbing polymeric materials to withstand the stresses of swelling. The surface-coating can break when the water-absorbing polymer particles swell or the surface-coating can break after the water-absorbing polymer particles having been in a fully swollen state for a certain period of time.

It is therefore desirable to find a method to make surface-coated water absorbing polymer particles with narrow particles size distribution and regular coating while improving the absorptive properties of the surface-coated water absorbing polymer particles.

SUMMARY OF THE INVENTION

The present invention provides a method for making surface-coated water-absorbing polymer particles in a microfluidic device. The microfluidic device comprises a first microfluidic channel conveying precursor water-absorbing polymer particles, a second microfluidic channel conveying a first coating solution, a third microfluidic channel conveying water-absorbing polymer particles coated with the first coating solution, a fourth microfluidic channel conveying a first non aqueous liquid, a first intersection between the first microfluidic channel and the second microfluidic channel, and a second intersection between the third microfluidic channel and the fourth microfluidic channel. The third microfluidic channel is in communication with the first intersection and the second intersection. The method comprises the steps of:

a) providing precursor water-absorbing polymer particles, the first coating solution and the first non aqueous liquid, b) feeding the precursor water-absorbing polymer particles in the first microfluidic channel of the microfluidic device, c) feeding the first coating solution in the second microfluidic channel of the microfluidic device, d) feeding the first non aqueous liquid in the fourth microfluidic channel of the microfluidic device, e) coating precursor water-absorbing polymer particles with the first coating solution at the first intersection and/or in the third microfluidic channel, f) conveying the precursor water-absorbing polymer particles coated with the first coating solution through the third microfluidic channel toward the second intersection, g) separating the precursor water-absorbing polymer particles coated with the first coating solution from each other with the first non aqueous liquid at the second intersection, and h) polymerizing the coated water-absorbing polymer particles to obtain surface-coated water-absorbing polymer particles, or i) crosslinking the coated water-absorbing polymer particles to obtain surface-coated water-absorbing polymer particles.

The invention also relates to the surface-coated water-absorbing polymer particles obtained by the method according to the invention wherein the diameter in dry state of the surface-coated water-absorbing polymer particles is increased from 1% to 30% based on the diameter in dry state of the precursor water-absorbing polymer particles.

The invention also relates to surface-coated water-absorbing polymer particles comprising a core and a coating layer having a largest caliper and a smallest caliper. The coating layer is formed onto the core from a first coating solution. The coating layer is uniformly distributed around the core.

The ratio of the smallest caliper to the largest caliper of the coating layer of the surface-coated water absorbing polymer particles is from 1:1 to 1:3 according to the staining test method described herein.

The invention also relates to an absorbent article comprising the surface-coated water-absorbing polymer particles obtained via the method described herein.

The microfluidic device enables to have surface-coated water-absorbing polymer particles with consistent quality, in terms of size distribution and with a relatively homogeneous caliper.

The microfluidic device allows having surface-coated water-absorbing polymer particles with a regular shape, in particular spherical shape. Having surface-coated water absorbing polymer particles with a regular shape may improve the pore volume of the gel bed formed by the distances between two surface-coated water-absorbing polymer particles and may improve the availability for incoming fluid. It reduces the risk of gel blocking.

Moreover, the surface-coated water-absorbing polymer particles may have a narrow particles size distribution. From one surface-coated water-absorbing polymer particles to another, the size of the particles may be consistent. Having surface-coated water-absorbing polymer particles with a narrow particles size distribution may lead to a higher porosity and higher pore connectivity. This effect improves the permeability of the surface-coated water-absorbing polymer particles.

The number of surface-coated water-absorbing polymer particles obtained via the microfluidic device may be significantly higher than the number of water-absorbing polymer particles without surface-coating obtained via the microfluidic device. Having a low amount of non surface-coating water-absorbing polymer particles avoids the creation of gel blocking thus yielding high permeability for fluid transport through the swollen gel bed.

Furthermore, the surface-coated water-absorbing polymer particles show good performance properties. Especially, the surface-coated water-absorbing polymer particles have a high permeability. Indeed, the surface-coated water-absorbing polymer particles have a coating layer that does not substantially rupture when the water-absorbing polymer particles swell under typical use-conditions. Therefore, the surface-coated water-absorbing particles do not deform to an unacceptable extent causing gel-blocking.

While having a high permeability, the surface-coated water-absorbing polymer particles have still a good absorption capacity.

DETAILED DESCRIPTION OF THE INVENTION

Definition

Figure 1:
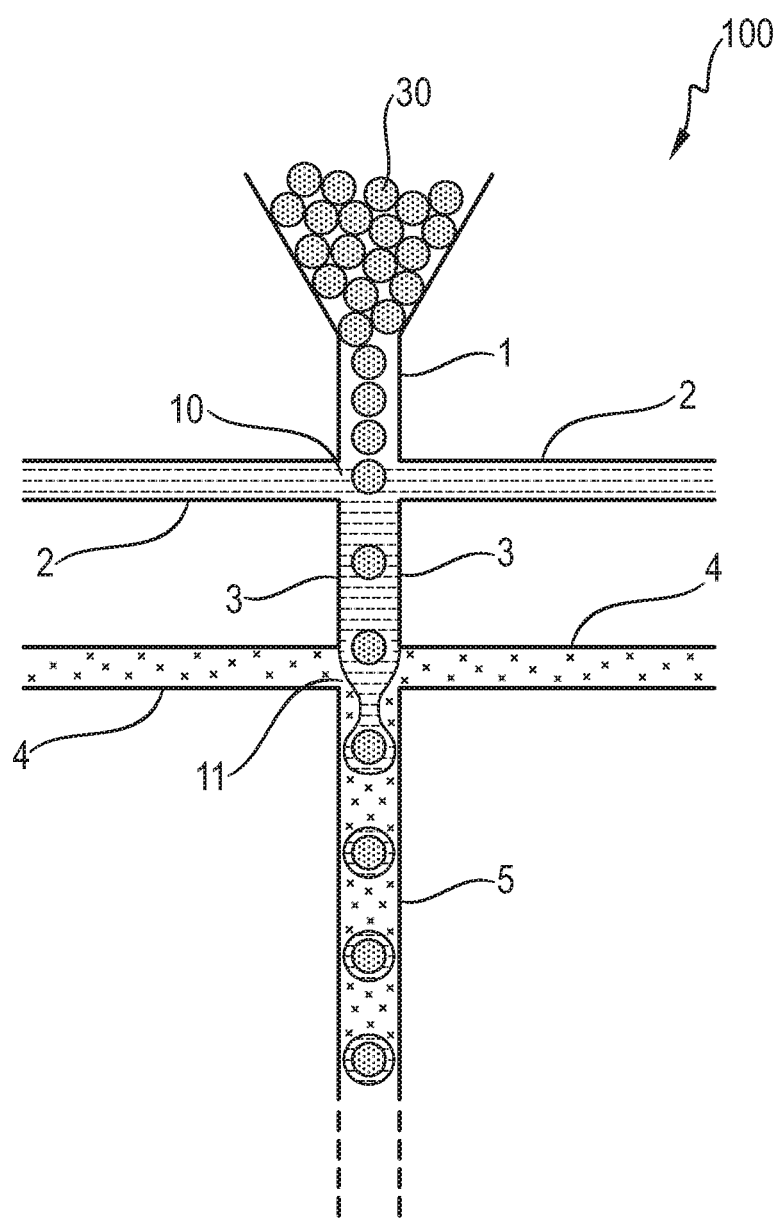
FIG. 1 is a schematic view of a microfluidic device in accordance with the present invention.

The term "Absorbent article" refers to devices that absorb and contain body exudates, and, more specifically, refers to devices that are placed against or in proximity to the body of the wearer to absorb and contain the various exudates discharged from the body. Absorbent articles may include diapers (baby diapers and diapers for adult incontinence), pants, inserts, feminine care absorbent articles such as sanitary napkins or pantiliners, and the like. The term "exudates" includes, but is not limited to, urine, blood, vaginal discharges, sweat and fecal matter. Preferred absorbent articles of the present invention are disposable absorbent articles, more preferably disposable diapers and disposable pants.

The term "Coating" includes partial coatings, whereby the outer surface of the particles are partially covered with a coating agent, homogeneous coatings, whereby the coating is present in a homogeneous amount per surface area of the particle, complete coatings, whereby substantially the complete surface of the particles is covered (and for example homogeneously) or whereby said coating agent forms a substantially complete network on said surface of said particles (and for example homogeneously), and homogeneous complete coatings.

"Disposable" is used in its ordinary sense to mean an article that is disposed or discarded after a limited number of usage over varying lengths of time, for example, less than 20 usages, less than 10 usages, less than 5 usages, or less than 2 usages. If the disposable absorbent article is a diaper, a pant, sanitary napkin, sanitary pad or wet wipe for personal hygiene use, the disposable absorbent article is most often intended to be disposed after single use.

"Diaper" and "pant" refers to an absorbent article generally worn by babies, infants and incontinent persons about the lower torso so as to encircle the waist and legs of the wearer and that is specifically adapted to receive and contain urinary and fecal waste. In a pant, the longitudinal edges of the first and second waist region are attached to each other to a pre-form waist opening and leg openings. A pant is placed in position on the wearer by inserting the wearer's legs into the leg openings and sliding the pant absorbent article into position about the wearer's lower torso. A pant may be preformed by any suitable technique including, but not limited to, joining together portions of the absorbent article using refastenable and/or non-refastenable bonds (e.g., seam, weld, adhesive, cohesive bond, fastener, etc.). A pant may be preformed anywhere along the circumference of the article (e.g., side fastened, front waist fastened). In a diaper, the waist opening and leg openings are only formed when the diaper is applied onto a wearer by (releasably) attaching the longitudinal edges of the first and second waist region to each other on both sides by a suitable fastening system.

"Comprise," "comprising," and "comprises" are open ended terms, each specifies the presence of what follows, e.g., a component, but does not preclude the presence of other features, e.g., elements, steps, components known in the art, or disclosed herein. These terms based on the verb "comprise" should be read as encompassing the narrower terms "consisting of" which excludes any element, step, or ingredient not specified and "consisting essentially of" which limits the scope of an element to the specified materials or steps and those that do not materially affect the way the element performs its function. Any preferred or exemplary embodiments described below are not limiting the scope of the claims, unless specifically indicated to do so. The words "typically", "normally", "advantageously" and the likes also qualify elements which are not intended to limit the scope of the claims unless specifically indicated to do so.

Surface-Coated Water-Absorbing Polymer Particles

The surface-coated water-absorbing polymer particles comprise precursor water-absorbing polymer particles that are subsequently coated with the first coating solution according to the method of the present invention.

The microfluidic device enables to have a large portion of surface-coated water-absorbing polymer particles with a narrow particles size distribution and with a homogenous coating around each particle. The term "portion of surface-coated water-absorbing polymer particles" means part in numbers of surface-coated water-absorbing polymer particles compared to the total number of surface-coated water-absorbing polymer particles.

The coating layer formed by the first coating solution may form a continuous coating layer around the precursor water-absorbing polymer particle and the coating layer may cover the entire surface of the precursor water-absorbing polymer particle. Thus, no regions of the precursor water-absorbing polymer particle may be exposed to the outside environment.

The coating layer and the surface-coating water-absorbing polymer particles are water permeable such as to allow a fast absorption of liquid into the precursor water-absorbing polymer particles.

Preferably, the first coating solution consists in dry state of not more than 50% by weight of the coating of the surface-coated water-absorbing polymer particles in dry state. Preferably, the first coating solution consists in dry state of 1% to 30% by weight, more preferably of 1% to 20% by weight, even more preferably of 5% to 15% by weight of the coating of the surface-coated water-absorbing polymer particles in dry state.

The first coating solution is applied such that the resulting coating layer in partially swollen state is relatively thin. The coating layer on the surface-coated water-absorbing polymer particles in dry state may have an average caliper from 1 to 100 μm. Preferably, the coating layer on the surface-coated water-absorbing polymer particles in dry state has an average caliper from 1 to 50 μm, more preferably from 1 to 20 μm or even more preferably from 2 to 10 μm.

The coating layer on the surface-coated water-absorbing polymer particles in the fully swollen state (in 0.9 wt % saline solution according to the staining test method described herein) may have an average caliper from 2 to 250 μm Preferably, the coating layer on the surface-coated water-absorbing polymer particles in the fully swollen state has an average caliper from 1 to 50 μm, more preferably from 1 to 20 μm according to the test method disclosed herein which uses staining the surface-coated water-absorbing polymer particles with 20 ppm Toluidine Blue O in 0.9% wt and 10% wt NaCl solution.

The diameter in dry state of the surface-coated water-absorbing polymer particles obtained by the method described herein may be increased from 1% to 30% of the precursor water-absorbing polymer particles diameter, more preferably from 5% to 20% of the precursor water-absorbing polymer particles diameter according to any conventional particles size analysis test method such as the use of the light microscopy (Keyence Digital microscope VHX5000) or the use of Scanning Electron Microscope (SEM).

Preferably, the resulting coating on the surface-coated water-absorbing polymer particles is substantially uniform. The average caliper of the coating layer of the surface-coated water-absorbing polymer particles may be such that the ratio of the smallest to largest caliper is between 1 to 1 and 1 to 5, preferably between 1 to 1 and 1 to 2 according to the test method disclosed herein which uses staining the surface-coated water-absorbing polymer particles with 20 ppm Toluidine Blue O in 0.9% wt and 10% wt NaCl solution.

After using the microfluidic method to obtain surface-coated water-absorbing polymer particles, some precursor water-absorbing polymer particles may not have been coated. However, at least 70% out of 100% of particles formed by the microfluidic process technology may be coated. Preferably, at least 80% out of 100% of particles formed by the microfluidic process technology are coated. More preferably, at least 90% out of 100% of particles formed by the microfluidic process technology are coated. Coating may be detected, e.g. via the staining test method described herein.

The surface-coated water-absorbing polymer particles may comprise two or more coating layers, obtainable by coating the surface-coated water-absorbing polymer particles once or more. This may be done with the first coating solution or with a second coating solution different from the first coating solution.

The average diameter of the surface-coated water-absorbing polymer particles in dry state may be from 30 μm to 3 mm, preferably from 30 μm to 1 mm according to any conventional particles size analysis test method such as the use of light microscopy (Keyence Digital microscope VHX5000), or standard PSD test method (EDANA method WSP 220.2-05).

Preferably, the surface-coated water-absorbing polymer particles obtained via the microfluidic device have substantially the same diameter. Preferably, more than 90% of the surface-coated water-absorbing polymer particles obtained via the microfluidic device have substantially the same diameter. The term "substantially" means the surface-coated water-absorbing polymer particles being compared have such close diameter as to be essentially the same as understood by one having ordinary skill in the art.

The relative variance of the diameter of different surface-coated water-absorbing polymer particles in the dry state obtained by the method described herein may be less than 50%, preferably less than 25%, more preferably less than 10%.

Preferably, the surface-coated water-absorbing polymer particles obtained in the microfluidic device have a narrow particles size distribution. The surface-coated water-absorbing polymer particles may have a relatively narrow range of particles size distribution in the dry state with the weight average particle size of the surface-coated water-absorbing polymer particles is from 50 µm to 800 µm, preferably from 100 µm to 600 µm, more preferably from 200 µm to 500 µm according to standard PSD test method (EDANA method WSP 220.2-05).

The surface-coated water-absorbing polymer particles may have a regular or irregular shape. More specifically, the surface-coated water-absorbing polymer particles may have a spherical shape or an ellipsoidal shape. Preferably, the surface-coated water-absorbing polymer particles have spherical shape or ellipsoidal shape.

The surface-coated water-absorbing polymer particles made according to the method herein may have a high permeability as measured by the Urine Permeability Measurement (UPM) test method described herein. The permeability of the surface coated water-absorbing polymer particle may be at least 5 UPM units, preferably at least 10 UPM units, more preferably at least 30 UPM units and even more preferably 50 UPM units as measured by the Urine Permeability Measurement (UPM) test method described herein where 1 UPM unit is $1 \times 10^{-7}$ (cm3·s)/g.

The surface-coated water-absorbing polymer particles made according to the method herein may have a high absorption capacity. The high absorption capacity of the surface-coated water-absorbing polymer particles may be at least 10 g/g, preferably at least 20 g/g, more preferably at least 30 g/g, even more preferably 35 g/g according to the CRC test method (EDANA method NWSP 241.0.R2).

The surface-coated water-absorbing polymer particles may be treated with a surface treatment.

The surface treatment may be done after the step of polymerizing or crosslinking the coated water-absorbing polymer particles to obtain surface-coated water-absorbing polymer particles.

Such surface treatment with one or more surface treatment agent(s) makes it possible to achieve additional effects, such as a reduced tendency to cake, improved processing properties or a further enhanced permeability.

The surface treatment may comprise water soluble polyvalent metal salts, water-insoluble metal phosphates and inorganic particles, for example silica, clay, or mica.

Preferably, water soluble polyvalent metal salts are aluminum sulfate, aluminum nitrate, aluminum chloride, potassium aluminum sulfate, sodium aluminum sulfate, magnesium sulfate, magnesium citrate, magnesium lactate, zirconium sulfate, zirconium lactate, iron lactate, iron citrate, calcium acetate, calcium propionate, calcium citrate, calcium lactate, strontium lactate, zinc lactate, zinc sulfate, zinc citrate, aluminum lactate, aluminum acetate, aluminum formiate, calcium formiate, strontium formiate, strontium acetate. They may be used as surface treatment for the precursor water-absorbing polymer particles in order to impart a high passive fluid transport (UPM) by homogeneously coating the surface of the precursor water-absorbing polymer particles.

Suitable water-insoluble metal phosphates may be selected from the group of pyrophosphates, hydrogen phosphates and phosphates of calcium, of magnesium, of strontium, of barium, of zinc, of iron, of aluminum, of titanium, of zirconium, of hafnium, of tin, of cerium, of scandium, of yttrium or of lanthanum, and also mixtures thereof.

Suitable inorganic particles may be applied as powders or aqueous dispersions. Inorganic particles may be selected from the group of silica, fumed silica, colloidal dispersed silica, titaniumdioxide, aluminum- and magnesiumoxide, zinc oxide, clay. Silica may be hydrophilic or hydrophobic. For example, silica is known in the art to improve the absorption speed of the surface-coated water-absorbing polymer particles.

The surface treatment may also be selected from the group of film-forming polymers and/or elastic polymers and/or elastic film-forming polymers. Such surface treatment may be applied in order to form a complete coating on the precursor water-absorbing polymer particles. The term 'film-forming' means that the respective polymer can readily be made into a film, i.e. layer or coating, upon evaporation of the solvent in which it is dissolved or dispersed. The polymer may for example be thermoplastic or crosslinked. Suitable film-forming polymers may exhibit elastic physical properties. The elastic and elastic film-forming agents/polymers suitable as coating agents herein are disclosed in U.S. Pat. No. 5,731,365 and in EP 0703265, and also in WO 2006/082242 and WO 2006/097389.

The present invention also relates to surface-coated water-absorbing polymer particles, each comprise a precursor water-absorbing polymer particle and a coating layer. The coating layer is formed onto and around the precursor water-absorbing polymer particle from the first coating solution.

The coating layer formed by the first coating solution may form a continuous coating layer around the precursor water-absorbing polymer particle of the surface-coated water-absorbing polymer particle and the coating layer may cover the entire surface of the precursor water-absorbing polymer particle. Thus, no regions of the precursor water-absorbing polymer particle of the surface-coated water-absorbing polymer particles may be exposed to the outside environment.

The coating layer on the surface-coated water-absorbing polymer particles in partially swollen state may have an average caliper from 1 to 100 µm according to the test method disclosed herein which uses staining the surface-coated water-absorbing polymer particles with 20 ppm Toluidine Blue O in 0.9% wt and 10% wt NaCl solution.

Preferably, the coating layer on the surface-coated water-absorbing polymer particles in dry state has an average caliper from 1 to 50 µm, more preferably from 1 to 20 µm or even more preferably from 2 to 10 µm.

The surface-coated water-absorbing polymer particles in partially swollen state may be defined according to the test method of staining the surface-coated water-absorbing polymer particles with 20 ppm Toluidine Blue O in 0.9% wt and 10% wt NaCl solution.

The coating layer on the surface-coated water-absorbing polymer particles in the fully swollen state may have an average caliper from 2 to 250 µm according to the test method disclosed herein which uses staining the surface-coated water-absorbing polymer particles with 20 ppm Toluidine Blue O in 0.9% wt and 10% wt NaCl solution.

Preferably, the coating layer on the surface-coated water-absorbing polymer particles in the fully swollen state has an average caliper from 1 to 50 µm, more preferably from 1 to 20 µm according to the test method disclosed herein which uses staining the surface-coated water-absorbing polymer particles with 20 ppm Toluidine Blue O in 0.9% wt and 10% wt NaCl solution.

The coating layer has a largest caliper and a smallest caliper. The ratio of the smallest caliper to the largest caliper of the coating layer of the surface-coated water absorbing polymer particles in partially swollen state is from 1:1 to 1:3 according to the staining test method disclosed herein. Preferably, the ratio of the smallest caliper to the largest caliper of the coating layer of the surface-coated water absorbing polymer particles in dry state is from 1:1 to 1:2 according to the staining test method disclosed herein.

The surface-coated water-absorbing polymer particles have a coating layer with the specific ratio defined above may have a relatively homogeneous caliper. Therefore, the surface-coated water-absorbing polymer particles may not substantially rupture when the precursor water-absorbing polymer particles swell under typical use-conditions. Thereby, the surface-coated water-absorbing polymer particles may not deform to an unacceptable extent causing gel-blocking. Having surface-coated water-absorbing polymer particles with a relatively homogeneous caliper may improve the pore volume of the gel bed formed by the distance between two surface-coated water-absorbing polymer particles and may improve the availability for incoming fluid.

The surface-coated water absorbing polymer particles having the specific ratio defined above may be obtained via the method of the present invention. The microfluidic device enables to have a homogenous coating around each particle.

Precursor Water-Absorbing Polymer Particles

The precursor water-absorbing polymer particles as used herein refer to crosslinked polymeric materials that can absorb at least 10 times their weight of an aqueous 0.9% saline solution as measured using the Centrifuge Retention Capacity test (EDANA method NW SP 241.0.R2). The precursor water-absorbing polymer particles are in particulate form so as to be flowable in the dry state. Preferred precursor water-absorbing polymer particles of the present invention are made of polyacrylic acid polymers. However, e.g. starch-based superabsorbent polymer particles are also comprised within the scope of the present invention.

Typically, these polymers are crosslinked polymers, preferably lightly crosslinked hydrophilic polymers. While these polymers may in general be non-ionic, cationic, zwitterionic or anionic, the preferred polymers are cationic or anionic.

Preferably, precursor water-absorbing polymer particles are acid polymers which contain a multiplicity of acid functional groups such as carboxylic acid groups or their salts, preferably sodium salts.

Preferably, the precursor superabsorbent polymer particles comprise crosslinked polymers of polyacrylic acids or their salts or polyacrylates or derivatives thereof.

The precursor water-absorbing polymer particles can be spherical shaped water-absorbing polymer particles or ellipsoidal shaped water-absorbing polymer particles or irregular shaped water-absorbing polymer particles. Preferably, the precursor water-absorbing polymer particles have a spherical or ellipsoid shape.

Preferably, precursor water-absorbing polymer particles are obtainable by polymerization of a monomer solution comprising
i) at least one ethylenically unsaturated acid-functional monomer,
ii) at least one crosslinker,
iii) if appropriate one or more ethylenically and/or allylically unsaturated monomers copolymerizable with i) and
iv) if appropriate one or more water-soluble polymers onto which the monomers i), ii) and if appropriate iii) can be at least partially grafted,
v) at least one polymerization initiator system,
wherein the base polymer obtained thereby is dried, classified and—if appropriate—is subsequently treated with
vi) at least one post-crosslinker to be post-crosslinked (i.e. surface crosslinked).

Useful monomers i) include for example ethylenically unsaturated carboxylic acids and their salts, such as acrylic acid, methacrylic acid, maleic acid, fumaric acid, tricarboxy ethylene, itaconic acid, ethylenically unsaturated phosphonic acid and ethylenically unsaturated sulfonic acid or their salts, or derivatives thereof, such as acrylamide with 2-acrylamido-2-methylpropane sulfonic acid, methacrylamide, acrylic esters and methacrylic esters.

Acrylic acid or its salts and methacrylic acid or its salts are particularly preferred monomers. Acrylic acid or its salts is most preferable.

The precursor water-absorbing polymer particles are crosslinked, i.e., the polymerization is carried out in the presence of compounds having two or more polymerizable groups which can be free-radically copolymerized into the polymer network. Useful crosslinkers ii) may include for example ethylene glycol dimethacrylate, diethylene glycol diacrylate, allyl methacrylate, trimethylolpropane triacrylate, triallylamine, tetraallyloxyethane as described in EP-A 530 438, di- and triacrylates as described in EP-A 547 847, EP-A 559 476, EP-A 632 068, WO 93/21237, WO 03/104299, WO 03/104300, WO 03/104301 and in the DE-A 103 31 450, mixed acrylates which, as well as acrylate groups, comprise further ethylenically unsaturated groups, as described in DE-A 103 31 456 and DE-A 103 55 401, or crosslinker mixtures as described for example in DE-A 195 43 368, DE-A 196 46 484, WO 90/15830 and WO 02/32962.

Preferably, the crosslinkers ii) are diacrylated, dimethacrylated, triacrylated or trimethacrylated multiply ethoxylated and/or propoxylated glycerols. Di- and/or triacrylates of 3- to 10-tuply ethoxylated glycerol are particularly advantageous. More preferably, the crosslinkers ii) are di- or triacrylates of 1- to 5-tuply ethoxylated and/or propoxylated glycerol.

Examples of ethylenically unsaturated monomers iii) which are copolymerizable with the monomers i) may be acrylamide, methacrylamide, crotonamide, dimethylaminoethyl methacrylate, dimethylaminoethyl acrylate, dimethylaminopropyl acrylate, diethylaminopropyl acrylate, dimethylaminobutyl acrylate, dimethylaminoethyl methacrylate, diethylaminoethyl methacrylate, dimethylaminoneopentyl acrylate and dimethylaminoneopentyl methacrylate.

Useful water-soluble polymers iv) may include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide, preferably polyvinyl alcohol and starch.

The preparation of a suitable base polymer and also further useful hydrophilic ethylenically unsaturated monomers i) are described in DE-A 199 41 423, EP-A 686 650, WO 01/45758 and WO 03/14300. The reaction is preferably carried out in a kneader as described for example in WO 01/38402, or on a belt reactor as described for example in EP-A-955 086.

Neutralizing agents can be used, such as alkali metal hydroxides, alkali metal oxides, alkali metal carbonates or alkali metal bicarbonates and also mixtures thereof. Neutralizing agents may be ammonia, or amines derivatives, such as ethanolamine, diethanolamine, triethanolamine or dimethylaminoethanolamine. Sodium and potassium can be used as alkali metal salts. Preferably, neutralizing agents are sodium hydroxide, sodium carbonate or sodium bicarbonate and also mixtures thereof. Typically, neutralization is achieved by admixing the neutralizing agent as an aqueous solution or as an aqueous dispersion or else as a molten or as a solid material. The acid groups of the base polymers obtained are typically 0-100 mol %, preferably 25-100 mol %, more preferably 65-90 mol % and most preferably 68-80 mol % neutralized.

A polymerization initiator system v) is used in order to initiate the polymerization.

This polymerization initiator system may be added in solid or liquid form, for example as a solution or dispersion in a liquid such as an aqueous liquid, e.g. water.

This polymerization initiator system may comprise more than one type of compound to initiate the polymerization, or it may comprise a single type of compound.

The polymerization initiator system may include an activator, such as an activator compound or for example heat or radiation, including light radiation. Alternatively, no activation may be needed.

The polymerization initiator system can be appropriately selected from conventional (e.g. radical) polymerization initiators (and optional catalysts). Materials which display good water dispersibility/solubility are preferred. The initiator compound(s) of the system include for example peroxides, hydroperoxides, hydrogen peroxide, persulfates, azo compounds and redox initiators. Useful organic peroxides are for example acetylacetone peroxide, methyl ethyl ketone peroxide, tert-butyl hydroperoxide, cumene hydroperoxide, tert-amyl perpivalate, tert-butyl perpivalate, tert-butyl perneohexanoate, tert-butyl perisobutyrate, tert-butyl per-2-ethylhexanoate, tert-butyl perisononanoate, tert-butyl permaleate, tert-butyl perbenzoate, di(2-ethylhexyl) peroxydicarbonate, dicyclohexyl peroxydicarbonate, di(4-tert-butylcyclohexyl) peroxydicarbonate, dimyristyl peroxydicarbonate, diacetyl peroxydicarbonate, allyl peresters, cumyl peroxyneodecanoate, tert-butyl per-3,5,5-tri-methylhexanoate, acetylcyclohexylsulfonyl peroxide, dilauryl peroxide, dibenzoyl peroxide and tert-amyl perneodecanoate. Preferred azo compounds include 2,2'-azobisisobutyronitrile, 2,2'-azobis(2,4-dimethylvaleronitrile) and 2,2'-azobis(4-methoxy-2,4-dimethyl-valeronitrile), especially water-soluble azo initiators, examples being 2,2'-azobis-{2-[1-(2-hydroxyethyl)-2-imidazolin-2-yl]propane}dihydrochloride, 2,2'-azobis-(2-amidinopropane)dihydrochloride, 2,2'-azobis[2-(2-imidazolin-2yl)propane] dihydrochloride and 2,2'-azobis[2-(5-methyl-2-imidazolin-2-yl)propane] dihydrochloride. Very particular preference is given to 2,2'-azobis[2-(2-imidazolin-2-yl)propane] dihydrochloride and 2,2'-azobis [2-(5-methyl-2-imidazolin-2yl)propane] dihydrochloride.

More particularly, the polymerization initiator system v) can also be persulfates such as sodium peroxodisulfate, potassium peroxodisulfate and ammonium peroxodisulfate; hydroperoxides such as t-butyl hydroperoxide and cumene hydroperoxide; and azo compounds such as 2,2'-azobis-2-amidinopropane hydrochloride, e.g. such as VA-044, V-50 and V-501 (all manufactured by Wako Pure Chemical Industries Ltd.), and mixtures of $Fe^{2+}$; and hydrogen peroxide, or hydrogen peroxide and ascorbic acid. A mixture of two or more polymerization initiators may be used, for example one of the class of azo-compounds and one of the class of peroxo or peroxide compounds. This is believed to ensure fast polymerization. As described in US2008/242817, the use of azo compound initiator or redox initiators is advantageous for directing the rate of polymerization.

The polymerization initiator system may be introduced at a level of at least 0.001% by weight of the polymerizable monomers, preferably at least 0.01%, more preferably at least 0.02%, up to 0.1%, preferably up to 0.05% by weight of the polymerizable monomers.

The polymerization rate can be controlled through the identity and amount of the polymerization initiator compound used and the temperature used.

A polymerization catalyst may also be present, such as for example TMEDA (N,N,N',N' tetramethylethylenediamine). The polymerization of the polymerizable monomers may be highly exothermic, and hence, the polymerization liquid may be cooled during polymerization.

The precursor water-absorbing polymer particles can be post-crosslinked. Useful post-crosslinkers vi) include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. Useful post-crosslinkers vi) are further said to include by DE-A 40 20 780 cyclic carbonates, by DE-A 198 07 502 2-oxazolidone and its derivatives, such as N-(2-hydroxyethyl)-2-oxazolidone, by DE-A 198 07 992 bis- and poly-2-oxazolidones, by DE-A 198 54 573 2-oxotetrahydro-1,3-oxazine and its derivatives, by DE-A 198 54 574 N-acyl-2-oxazolidones, by DE-A 102 04 937 cyclic ureas, by DE-A 103 34 584 bicyclic amide acetals, by EP-A 1 199 327 oxetanes and cyclic ureas and by WO 03/031482 morpholine-2,3-dione and its derivatives.

Post-crosslinking is typically carried out by spraying a solution of the post-crosslinker onto the base polymer or the dry base-polymeric particles. Spraying is followed by thermal drying, and the post-crosslinking reaction can take place not only before but also during or after drying. Preferred post-crosslinkers vi) are amide acetals, carbamic esters, polyhydric alcohols like diols or polyols, cyclic carbonates or bisoxazolines.

At least one post-crosslinker vi) may be used in an amount of about 1.50 wt. % or less, preferably not more than 0.50% by weight, more preferably not more than 0.30% by weight and most preferably in the range from 0.001% and 0.15% by weight based on the dry weight of the precursor water-absorbing polymer particles.

The aqueous post-crosslinking solution, as well as the at least one post-crosslinker vi), can further comprise a co-solvent. Co-solvents which are technically highly useful are $C_1$-$C_6$-alcohols, such as methanol, ethanol, n-propanol, isopropanol, n-butanol, sec-butanol, tert-butanol or 2-methyl-1-propanol, $C_2$-$C_5$-diols, such as ethylene glycol, 1,2-propylene glycol, 1,3-propanediol or 1,4-butanediol, ketones, such as acetone, or carboxylic esters, such as ethyl acetate.

The total amount of post-crosslinking solution based on the base polymer may be in the range from 0.3% to 15% by weight and preferably in the range from 2% to 6% by weight.

The precursor water-absorbing polymer particles can have in the dry state a particle size distribution in the range from 45 µm to 1000 µm according to standard PSD test method (EDANA method WSP 220.2-05). Preferably precursor water-absorbing polymer particles have a particle size distribution in the range from 45 µm to 850 µm, more preferably from 100 µm to 850 µm, more preferably 150-710 µm, more preferably 150-500 µm or even more preferably 150-300 µm according to standard PSD test method (EDANA method WSP 220.2-05).

The precursor water-absorbing polymer particles may have, prior to coating, an absorption capacity of at least 20 g/g, preferably of at least 30 g/g, more preferably, of at least 35 g/g, even more preferably of at least 40 g/g according to the CRC test method (EDANA method NWSP 241.0.R2).

The precursor water-absorbing polymer particles may be dried or swollen before being coated with the first coating solution. For example, the X-load of the precursor water-absorbing polymer particles before being coated with the first coating solution may be from 1 g/g to 20 g/g of aqueous liquid by weight of the precursor water-absorbing polymer particles in dry state, preferably from 0.3 to 10 g/g by weight, more preferably from 0.3 to 5 g/g by weight of the precursor water-absorbing polymer particles in dry state. The precursor water-absorbing polymer particles which are pre-swollen before being coated with the first coating solution may resist deformation longer when than are in contact with liquid than dry precursor water-absorbing polymer particles coated with the first coating solution. Therefore, the surface-coated water-absorbing polymer particles comprising pre-swollen precursor water-absorbing polymer particles may resist deformation longer allowing to achieve potentially higher final absorption capacity and to limit the break of the surface-coating.

First Coating Solution

The first coating solution may comprise particles such as inorganic solids particles, and either polymerizable monomers and/or oligomers, or crosslinkable polymers.

When the first coating solution comprises crosslinkable polymers and particles such as inorganic solids particles, the first coating solution also comprises a second type of crosslinkers.

Inorganic solids particles may be clay platelets. The clay platelets may be dispersed in an acidic polymerization liquid with carboxylic acid monomers and/or carboxylate monomers, or oligomers thereof, which form polycarboxylic acid/polycarboxylate polymers.

The first coating solution may be a dispersion or solution of compounds in a carrier liquid. In particular, the first coating solution may comprise homogeneously dispersed clay platelets with opposing basal platelet surfaces and platelet edges; and dissolved or homogeneously dispersed therein polymerizable monomers comprising a carboxylic acid group and/or carboxylate group, and/or polymerizable oligomers of one or more of the said monomers or crosslinkable polymers.

Clay and Clay Platelets

The first coating solution may comprise clay dispersed as platelets in an acidic aqueous liquid. The clay platelets in the acidic aqueous liquid are preferably homogeneously dispersed, e.g. so that there is no significant aggregation/flocculation of the clay platelets (e.g. just prior to polymerization, e.g., at the temperature/pressure conditions of polymerization). Clay platelets have edge surfaces and opposing basal platelet surfaces, also referred to as "surfaces" and platelet edge surfaces, and also referred to as "edges".

The clay platelets may be surface and/or edge-modified. This ensures that the clay platelets are dispersible as platelets in the acidic aqueous liquid, i.e. comprising the polymerizable monomers or oligomers with carboxylic acid or carboxylate group(s). In particular when the clay platelets are small, e.g. they have a low aspect ratio, e.g. of 300 or less or for example 200 or less, and/or when high shear mixing is an issue, the aggregation in acid liquids may be problematic and the edge modification may be very beneficial.

The clay platelets and the surface and/or edge-modified clay platelets in the polymerization liquid, e.g. prior to the polymerization reaction and during polymerization may for example have a largest particle size dimension (length) of less than 800 nm, preferably less than 500, preferably 300 nm or less, for example 200 nm or less, or 100 nm or less; and for example said largest particle size dimension (length) being at least 5 nm, or at least 10 nm, or at least 20 nm according to the use of X-ray microscopy, for example, the use of Xradia 810 Ultra 3D X-ray Microscope commercialized by Zeiss or which may be determined via removal of a micro-slice of the water-absorbing polymer particles (via a ultramicrotome) which is then subjected to a cryo-TEM methods, known in the art or by the use of the dynamic light scattering test method.

The dynamic light scattering test method is described in the article: Karpovich, A et al, "Determination of dimensions of exfoliating materials in aqueous suspensions", MethodsX, 2016, 3, 19-24. NMR relaxometry test method may also be used and is described in the same article above.

When the clay platelets have a large size dimension, it may be beneficial to break the larger size clay platelets by using an ultrasonic treatment before assessing their largest particle size dimension as described above.

The clay platelets and the surface and/or edge-modified clay platelets in said liquid, e.g. prior to the polymerization reaction and during polymerization, may for example have an aspect ratio of 300 or less, or 200 or less or 100 or less. The aspect ratio of clay is generally more than 5, or more than 10.

The aspect ratio of clay platelet is the ratio of the largest dimension and the lowest dimension, orthogonal to it, of the clay platelet.

In the obtained surface-coated water-absorbing polymer particles, the clay platelets may be present as individual platelets or may be present as small aggregates of, for example, of 2 to 5 clay platelets which may be determined via removal of a micro-slice of the surface-coated water-absorbing polymer particles (via a ultramicrotome) and submitting this to a cryo-TEM methods, known in the art or which may be determined via dynamic light scattering test method.

The clay may be purified before surface-modification and/or edge-modification, e.g. to remove metals etc., by methods known in the art (and referred to below).

For example, the clay to be modified may be a di-octahedral or tri-octahedral clay.

Examples of suitable clays to be modified are selected in the group consisting of kaolinite such as kaolin, illite such as glauconite, or smectite or montmorillonite including hectorite, laponite (i.e. synthetic clay), saponite or vermiculite or mixtures thereof.

Preferably, the clays are montmorillonite, hectorite or laponite.

These clays are often referred to as water swelling; however, it should be noted that, in the embodiment herein the clays are present as substantially individual clay platelets and then, they are no longer water swelling.

Surface and/or Edge Modification and Modification Compounds and Resulting Surface and/or Edge Modified Clay The clay in the first coating solution may have modified basal surface or "surfaces" and/or modified edges. This may be done prior to addition of the polymerizable monomers and/or oligomers or crosslinkable polymers, or simultaneously with addition of the polymerizable monomers and/or oligomers or crosslinkable polymers in the first coating solution. The surface and/or edge modification may be done prior to addition of the polymerizable monomers and/or oligomers or crosslinkable polymers (e.g. prior to making the aqueous liquid acidic). To obtain the surface and/or edge-modified clay, the clay is for example dispersed in a liquid that comprises the surface and/or edge modification compound(s), and/or the clay is dispersed in a liquid, and the modification compound(s) may then be added to the dispersion, optionally also as solution or dispersion.

The ratio of clay to surface and/or edge modification compound may for example be within the range of 1:1 to 100:1 (by weight, based on the weight of dry clay and dry edge and/or surface modification compound(s)).

In the following, the surface and/or edge modification compounds are described as they are before addition to the clay.

Edge Modification Compound(s)

When modifying the edges of the clay, the exchangeable cations of the clay edges are replaced by the edge modification compound(s). Then, typically, the point of zero charge of the clay edges is either shifted to a lower pH value, or the edge charge is made pH-independently neutral or pH-independently negative. Thus, the edge-modification compound(s) may be a compound that, when bonded to the edge of the clay platelets, makes the edge pH independently neutral or negative, or neutral of negative at the pH of the liquid.

In addition, or alternatively, the edge modification compounds may be a compound, which hinders and reduces aggregation of clay platelets.

The edge modification compound(s) may consist of one or more phosphorylation compounds. The phosphorylation compound(s) may be selected from the group consisting of: phosphate salts and/or derivatives thereof and/or acids forms thereof condensed phosphate salts, and/or derivatives thereof and/or acids forms thereof; phosponic acid, derivatives thereof and salts thereof and combinations thereof. For example, sodium pyrophosphate decahydrate may be suitably used.

Organo-Phosphor Derivatives May Also be Useful.

The edge modification compound(s) may consist of one or more silanization compounds (also referred to as: silane compound).

The silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, N-Alkyls, Alkenes, alkenyls; and b) Alkoxy, hydrogen, toluenesulfonyl, sulfonyl containing moieties, chloride, halide; and c) hydroxy, carboxy-containing moieties, epoxy-containing moieties, provided that at least one moieties are selected from the subgroup b) or subgroup c) and that not more than three moieties are selected from said subgroup a).

Preferably, the silanization compound may be an organo silane compound, e.g. of the formula: $SiR^{I}R^{II}R^{III}R^{IV}$, whereby the moieties $R^{I}$, $R^{II}$, $R^{III}$, $R^{IV}$ are each selected from the group consisting of the subgroups: a) Alkyl, Aryl, N-Alkyls, Alkenes, alkenyls; and b) Alkoxy, hydrogen, toluenesulfonyl, sulfonyl containing moieties, chloride, halide; and c) hydroxy, carboxy-containing moieties, epoxy-containing moieties, provided that at least from one to three moieties are selected from the subgroup a) and that at least one moieties are selected from the subgroup b) or subgroup c).

It may be beneficial that at least one of said moieties $R^{I}$, $R^{II}$, $R^{III}$, $R^{IV}$ is a moiety that is suitable to bond to the polymerizable monomer or polymerizable oligomer. For example, at least one of said moieties is an unsaturated moiety, such as vinyl. Preferably, the edge modification compound(s) is a silanization compound such as 7-Octenyldimethylmethoxysilane.

The edge modification compound(s) may consist of one or more fluorination compounds. Preferably, the edge modification compound(s) include fluoride salt, e.g. MF. Preferably, the counterion M is a mono-valent counterion, such as sodium or ammonium.

The edge modification compound(s) may be a compound that sterically hinders said platelet edges in order to reduce the risk of aggregation of the clay platelets in the acidic liquid, in addition to modifying the charge of the edges of the clay.

The edge modification compound(s) may have at least one moiety of at least 10 angstrom (A) or at least 15 angstrom, or at least 20 angstrom. Preferably the edge modification compound(s) have at least a moiety with a carbon chain of at least 6 carbon atoms, or at least 9 carbon atoms or at least 12 carbon atoms.

Other compounds to modify the edges of the clay include epoxides. For example polyether clays can be formed.

The edge-modification compound, in particular those described above as phosphorization, silanization or fluorination compounds, may have a further moiety or moieties that can ionically or covalently bind to the monomer or oligomer, or the polymer formed; for example, the edge modification compound may have one or more unsaturated moieties (e.g. with C=C group), and/or one or more moieties that can form an ester or amide bond with the carboxyl group of the monomer, oligomer or polymer thereof, such as an oligo-ether or polyether moiety. Then, the edge modification compound not only binds to the edge of the clay platelet, but the compound(s) can also ionically or covalently bind to the polymers.

The clay platelets may not only be edge-modified to ensure homogeneous dispersion, but the edge modification may further serve to strongly bind to the polymers, e.g. covalently/ionically.

Surface Modification Compound(s)

The surface modification compound(s) may be a compound that has a cationic moiety (and/or: cationic at the pH of the liquid herein and reaction herein), that can bind to the negatively charged basal surface of the clay platelet. The surface modified clay may have surface(s) that are neutral (at the pH of the liquid).

The surface modification compound(s) may comprise an alkylated nitrogen moiety, or alkoxylated nitrogen moiety, including for example linear, branched or cyclic amino-, ammonium-compounds. A majority of the moieties may be cationic at the pH of the reaction liquid/reaction.

The surface modification compound(s) may have one or more moieties selected from amines or imines, including derivatives thereof, such as diamines or diimines and/or ethylene or poly- or oligo-ethylene derivatives thereof, including hexamethylene diamine and derivatives thereof, ethylendiamine and derivatives thereof, oligo-alkyleneimine and derivatives thereof, such as linear or branched polyethyleneimine, olig-etheramines and derivatives thereof, linear or branched amides, or mixtures thereof.

The surface modification compound(s) may have an acryl amide moiety. The surface modification compound(s) may have a urethane moiety (bond by hydrogen bonding to the negative basal surface) or further modifications thereof. Preferably, the surface modification compound(s) may have a cationically modified urethane moiety.

Especially preferred are moieties selected from linear or branched polyethyleneimine, hexamethylene diamine or ethylendiamine, or derivatives of any of these, or mixtures thereof.

The surface modification compound(s) may also be a cationically modified oligo- or poly-saccharides, or derivative thereof.

In addition, the surface modification compound(s) may have one or more further moiety that is or are hydrophilic. This can aid dispersion of the surface-modified clay in the reaction liquid and/or can further enhance the hydrophilicity, and hence affinity for hydrophilic fluids (e.g. urine, blood, saline water), of the surface-coated water-absorbing polymer particles. This may for example be anionic moiety, or —OH. Preferably, the surface modification compound(s) has at least one moiety that is an alkoxylated moiety, carboxylated moiety, or sulfonated moiety, or sulfated moiety, to further improve hydrophilicity.

The surface modification compound(s) may be such that, when chemically bound to the clay surfaces, they introduce a sterically hindering moiety (s), which hinders and hence reduces aggregation of clay platelets. Hence, the surface modification compound(s) may have a moiety that is sterically hindering. Preferably, the surface modification compound(s) has one or more moieties that can provide sterical hindrance, having at least 6 Carbon atoms, and/or a length of at least 10 angstrom, or at least 15 angstrom. Preferably, the surface modification compound(s) has an oligomer chain moiety.

For example, the surface modification compound(s) may have oligo-alkyleneoxide (AO) moiety, such as a oligo-ethyleneoxide (EO) moiety, with an average number of AO (e.g. EO)-repeating units of at least 2 or at least 5 or at least 10, and up to 100, or up to 60 or up to 40. Preferably, the surface modification compound(s) has at least a moiety that is an oligo-ethoxylate with a number of 2 to 40 repeating units.

The surface modification compound(s), in particular those with a cationic group as described above, may have a further moiety or moieties that can ionically or covalently bind to the monomer or oligomer, or the polymer formed thereby; for example, the surface modification compound may have one or more unsaturated moieties (e.g. with C=C group), and/or one or more moieties that can form an ester or amide bond with the carboxyl group of the monomer, oligomer or polymer thereof, such as an oligo-ether or polyether moiety. Then, the surface modification compound not only binds to the surface of the clay platelet, but the compound(s) can also ionically or covalently bind to the polymers. Thus, the clay platelets are not only surface-modified to ensure homogeneous dispersion (and hence homogeneous incorporation in the final polymers), but the surface modification further serves to strongly bind to the polymers, e.g. covalently/ionically. The surface modification compound described herein above, e.g. with a cationic group, may for example comprise contain a polymerizable moiety, such as an alkylene, e.g. ethylene; and/or the unsaturated moiety may for example be an ester of acrylic acid, and/or an alkylated derivatives of acrylic acid, such as methacrylic acid.

It may be useful to apply during the surface and/or edge modification step and/or during the preparation of the first coating solution, (prior to commencement of the polymerization step or the crosslinking step) an ultrasonic treatment step, and/or mixing step; preferred is the application of a (e.g. high) shear mixing. For example, a Y-Tron mixer can be used. The exfoliation of the clay may also be affected by use of high-shear mixers, (such as CB Loedige mixers, Schugi mixers, Littleford mixers, Drais mixers). The tip speed of any such mixers may for example be from at least 20 ms$^{-1}$, or at least 30 ms$^{-1}$ to for example 45 or 40 or 35 ms$^{-1}$.

The surface and/or edge modification of the clay platelets may be done in any liquid. It may for example be done in water. Alternatively, the surface and/or edge modification may be done in the absence of water, e.g. preferably in an anhydrous liquid, e.g. anhydrous liquid with a dielectric constant larger than 40 preferentially more than 50, for example propylene carbonate, ethylene carbonate, etc.

The first coating solution may comprise clays which may be mixed with the polymerizable monomers and/or oligomers or crosslinkable polymers and simultaneously with the surface and/or edge modification compound(s). However, the first coating solution may comprise clays that are modified prior to mixing with the acidic solution of the polymerizable monomers and/or oligomers or crosslinkable polymers. Preferably, the surface and/or edge modification compound(s) modify the clay prior to addition to the first coating solution. It may be preferred to modify the clay's surfaces and/or edge, and then to wash the resulting modified clay, and/or filtrate and or/submit to dialysis the modified clay, prior to addition to the first coating solution that may comprise polymerizable monomers and/or oligomers.

The clay dispersion and/or clay modification may be at temperatures around 15-25° C., or optionally under heating to a temperature above 40° C., or above 45° C. or above 50° C., for example up to 90° C. or up to 70° C. or up to 60° C.

The liquid phase of the first coating solution comprises at least water, and it may optionally comprise other, e.g. organic, liquids, or it may consist of water. Highly preferred may be that the liquid phase comprises at least 80% by weight of water, preferably at least 90% or even 100% by weight of water.

The first coating solution can be purged with inert gas prior to the start of the polymerization, and optionally during polymerization.

An organic crosslinker (i.e. not clay containing) may be added to the first coating solution, such as organic crosslinkers known in the art. For example, typical crosslinkers are di- or poly-functional monomers, having two or more groups that can be polymerized, such as N,N'-methylenebisacrylamide, trimethylolpropane triacrylate, ethylene glycol di(meth)acrylate, or triallylamine Polymerizable Monomers and/or Oligomers or Crosslinkable Polymers The first coating solution may comprise polymerizable monomers (referred to as monomers), and/or polymerizable oligomers of the monomer(s) (e.g. oligomers having between 2 and typically 5000 polymerized monomers). In order to be polymerizable, the monomers and/or the oligomers may comprise a polymerizable moiety, such as a C=C moiety. Preferably, the monomer have a single polymerizable moiety, such as a single C=C moiety.

Preferably, monomers are used in said polymerization solution.

The polymerizable monomers and/or the oligomers may have one or more carboxylic acid and/or carboxylate moieties. For example, suitable monomers may be acrylic acid and/or acrylate monomers.

Preferably, the polymerizable monomers and/or oligomers comprise polymerizable monomers and/or oligomers of acrylic acids or their salts or acrylates or derivatives thereof.

The polymerizable monomers and/or oligomers may render the aqueous liquid acidic, i.e. having a pH of 6 or less, typically below 6, or preferably 5 or below 5.

The polymerizable monomers and/or oligomers may be neutralized or partially neutralized in the polymerization liquid. For example, the monomers or oligomers may comprise a carboxylate, (e.g. acrylate) group with a cation counterion. For example, the monomers (or oligomer) may be a carboxylate (e.g. acrylate) salt. The counter ion is typically sodium.

At least 20 mol % by weight (based on total of monomers or oligomers) of the polymerizable monomers and/or of the oligomers may be neutralized, e.g. having salt counterion. At least 40 mol %, or at least 50 mol % or at least 60 mol %, or at least 80 mol %, or at least 100 mol % of the polymerizable monomers and/or of the oligomers may be neutralized.

Alternatively, the first coating solution may comprise crosslinkable polymers. Preferably, the first coating solution comprises crosslinkable polymers. The crosslinkable polymers may include polyvinyl alcohol, polyvinylpyrrolidone, starch, starch derivatives, polyglycols, polyacrylic acids, polyvinylamine or polyallylamine, partially hydrolysed polyvinylformamide or polyvinylacetamide. Preferably, the crosslinkable polymers are polyacrylic acids or their salts or polyacrylates or derivatives thereof.

The crosslinkable polymers may have a weight average molecular weight determined by gel permeability chromatography of more than 8,000 g/mol, preferably within the range of 10,000 g/mol to 1,000,000 g/mol, more preferably within the range of 50,000 to about 750,000 g/mol and even more preferably within the range of 90,000 to 700,000 g/mol.

Second Type of Crosslinkers

The first coating solution may comprise a second type of crosslinkers. The second type of crosslinkers may include compounds comprising two or more groups capable of forming covalent bonds with the carboxylate groups of the polymers. Useful compounds include for example alkoxysilyl compounds, polyaziridines, polyamines, polyamidoamines, di- or polyglycidyl compounds as described in EP-A 083 022, EP-A 543 303 and EP-A 937 736, polyhydric alcohols as described in DE-C 33 14 019. A second type of crosslinkers may include the compounds from DE-A 40 20 780 cyclic carbonates, from DE-A 198 07 502 2-oxazolidone and its derivatives, such as N-(2-hydroxyethyl)-2-oxazolidone, from DE-A 198 07 992 bis- and poly-2-oxazolidones, from DE-A 198 54 573 2-oxotetrahydro-1,3-oxazine and its derivatives, from DE-A 198 54 574 N-acyl-2-oxazolidones, from DE-A 102 04 937 cyclic ureas, from DE-A 103 34 584 bicyclic amide acetals, from EP-A 1 199 327 oxetanes and cyclic ureas and from WO 03/031482 morpholine-2,3-dione and its derivatives.

Preferred second type of crosslinkers are amide acetals, carbamic esters, polyhydric alcohols like diols or polyols, cyclic carbonates, bisoxazolines, epoxides or Glycidyl Ethers such as Ethylene Glycol Diglycidyl Ether.

Preferred second type of crosslinkers are Glycidyl Ethers such as Ethylene Glycol Diglycidyl Ether.

When the first coating solution comprises a second type of crosslinkers, the first coating solution also comprises crosslinkable polymers.

Preferably, the first coating solution comprises a second type of crosslinkers with crosslinkable polymers.

Preferably, the first coating solution comprises Glycidyl Ethers such as Ethylene Glycol Diglycidyl Ether with crosslinkable polymers.

The first coating solution can comprise the second type of crosslinkers in a quantity within the range of 0.001 wt. % to 30 wt. %, preferably within the range of 0.01 wt. % to 15 wt. %, more preferably within the range of 0.02 wt. % to 7 wt. % based on the weight of the solution.

The first coating solution comprising inorganic solid particles and polymerizable monomers and/or oligomers, or crosslinkable polymers may have a viscosity determined according to ASTM 1824/90 at about 20° C. within a range of 25 mPa·s to 50,000 mPa·s, preferably within a range of 25 mPa·s to 20,000 mPa·s, more preferably within a range of 25 mPa·s to 5,000 mPa·s.

The first coating solution may comprise from 0.1 to 10 wt % of clay platelets with modified surfaces and/or edges, from 5 to 95 weight % of water; from 5 to 95 wt. % of polymerizable monomers and/or oligomers, from 0.001 to 10 wt. % of organic crosslinkers, optionally a dispersing aid, and from 0.001 to 5 wt. % of polymerization initiator to start the polymerization.

Alternatively, the first coating solution may comprise from 0.1 to 10 wt % of clay platelets with modified surfaces and/or edges, from 5 to 95 weight % of water; from 5 to 95 weight % of crosslinkable polymers, from 0.001 to 10 weight % of a second type of crosslinkers and optionally a dispersing aid.

Polymerization or Crosslinking Step

When the first coating solution comprises polymerizable monomers and/or oligomers, the first coating solution may comprise a polymerization initiator system in order to initiate the polymerization step. The polymerization initiator system may be activated by applying heat (at a temperature of 120° C. or higher than 120° C.) and/or radiation onto the microfluidic device when the polymerization will be initiated.

This polymerization initiator system may be added in solid or liquid form, for example as a solution or dispersion in a liquid such as an aqueous liquid, e.g. water.

This polymerization initiator system may comprise more than one type of compound to initiate the polymerization, or it may comprise a single type of compound.

The polymerization initiator system may include an activator, such as an activator compound or for example heat or radiation, including light radiation. Alternatively, no activation may be needed.

The polymerization initiator system can be appropriately selected from conventional (e.g. radical) polymerization initiators (and optional catalysts). The description of the polymerization initiator system is identical to the description given above for the polymerization initiator system of the precursor water-absorbing polymer particles.

The solid content of the first coating solution may be from 16% to 70% by weight compared to the total weight of the first coating solution.

If desired, the polymerization step can be followed by a drying step, e.g. at temperatures of e.g. more than 50° C., more than 100° C., more than 120° C., more than 180° C. or more than 200° C. or preferably of 100° C. to 150° C.

Alternatively, if the first coating solution comprises crosslinkable polymers and a second type of crosslinkers, a polymerization step may not be necessary. For example, a radical polymerization step may not be necessary.

If the first coating solution comprises crosslinkable polymers and a second type of crosslinkers, a crosslinking step follows step g) of the method described herein. The crosslinking step may be a heating step at a temperature of 120° C. or higher than 120° C. or a drying step.

If desired, crosslinking step can be followed by a drying step, for example, at temperatures of e.g. more than 50° C., more than 100° C., more than 120° C., more than 180° C. or more than 200° C. or preferably of 100° C. to 150° C.

The First Non Aqueous Liquid

The first non aqueous liquid can be a mixture of non-aqueous liquid and surfactants.

The first non-aqueous liquid of the invention preferably have a viscosity of less than or equal to 2 Pa·s, better less than or equal to 1 Pa·s and even better less than or equal to 0.1 Pa·s at a temperature of 25° C. and at a shear rate of 1 $s^{-1}$.

The first non-aqueous liquid may be selected from the group consisting of hydrocarbon oil, liquid fatty alcohol, fluorinated oil and silicone oil.

The term "hydrocarbon oil" means a hydrocarbon composed solely of carbon and hydrogen atoms, which is liquid at room temperature (25° C.) and at atmospheric pressure (760 mmHg; i.e. $1.013 \times 10^5$ Pa).

More particularly, the liquid hydrocarbons are chosen from:
- linear or branched, optionally cyclic, $C_6$-$C_{16}$ lower alkanes. Examples that may be mentioned include hexane, undecane, dodecane, tridecane, and isoparaffins, for instance isohexadecane, isododecane and isodecane.
- linear or branched hydrocarbons of mineral, animal or synthetic origin with more than 16 carbon atoms, such as volatile or non-volatile liquid paraffins and derivatives thereof, petroleum jelly, liquid petroleum jelly, polydecenes, hydrogenated polyisobutene such as Parleam®, and squalane.

The term "liquid fatty alcohol" means a non-glycerolated and non-oxyalkylenated fatty alcohol that is liquid at room temperature (25° C.) and at atmospheric pressure (760 mmHg; i.e. $1.013 \times 10^5$ Pa).

Preferably, the liquid fatty alcohols of the invention comprise from 8 to 30 carbon atoms.

The liquid fatty alcohols of the invention may be saturated or unsaturated. The saturated liquid fatty alcohols are preferably branched. They may optionally comprise in their structure at least one aromatic or non-aromatic ring. They are preferably acyclic.

More particularly, the liquid saturated fatty alcohols of the invention are chosen from dodecanol, octyldodecanol, isostearyl alcohol and 2-hexyldecanol. Preferably, the liquid saturated fatty alcohol of the invention is octyldodecanol.

The term "fluorinated oil" means a non-glycerolated and non-oxyalkylenated fatty alcohol that is liquid at room temperature (25° C.) and at atmospheric pressure (760 mmHg; i.e. $1.013 \times 10^5$ Pa).

Preferably, the fluorinated oil is selected from the group consisting of perfluorinated oil, the hydrofluorinated oil, the fluorocarbon oil such FC40 commercialized by 3M under the designation Fluorinert®.

The term "silicone oil" means an organopolysiloxane that is liquid at ordinary temperature (25° C.) and at atmospheric pressure (760 mmHg; i.e. $1.013 \times 10^5$ Pa).

Preferably, the silicone oil is chosen from liquid polydialkylsiloxanes, especially liquid polydimethylsiloxanes (PDMSs) and liquid polyorganosiloxanes comprising at least one aryl group.

Suitable non-aqueous liquids may include DC200, D40, D80, D100, Isopar G or Isopar H, PDMS, dodecanol.

The surfactants may be selected from the group consisting of amphiphilic surfactants with perfluoropolyether chains or perfluoroalkyl chains and hydrophilic head groups.

Preferably, the surfactants of the first non aqueous liquid are block copolymers of perfluoropolyether and polyethylenoxide. Examples of surfactants used in the method described herein may be block copolymer ABIL EM90 commercialized by Evonik, block copolymer PGP R90 commercialized by Danisco and KRYTOX 157 FLS commercialized by DuPont.

The Microfluidic Device

The microfluidic device may be any apparatus commercially available or described in the literature that is suitable for making surface-coated water-absorbing polymer particles.

The precursor water-absorbing polymer particles coated with the first coating solution may be obtained in the microfluidic device by the techniques selected from the group consisting of hydrodynamic flow focusing, coaxial shear flow, crossflow shear in cross junction, coflow junction and T-junction microchannel geometries.

According to FIG. 1, the microfluidic device 100 comprises a first microfluidic channel 1 conveying precursor water-absorbing polymer particles, a second microfluidic channel 2 conveying a first coating solution, a third microfluidic channel 3 conveying precursor water-absorbing polymer particles coated with the first coating solution and a fourth microfluidic channel 4 conveying a first non aqueous liquid.

The microfluidic device 100 comprises a first intersection 10 between the first microfluidic channel 1 and the second microfluidic channel 2, and a second intersection 11 between the third microfluidic channel 3 and the fourth microfluidic channel 4. The third microfluidic channel 3 is in communication with the first intersection 10 and the second intersection 11.

The first microfluidic channel 1 and the second microfluidic channel 2 that intersect at the first intersection 10 are at right angles or not at right angles.

Preferably, the first microfluidic channel 1 and the second microfluidic channel 2 that intersect at the first intersection 10 are at right angles.

The third microfluidic channel 3 and the fourth microfluidic channel 4 that intersect at the second intersection 11 are at right angles or not at right angles.

Preferably, the third microfluidic channel 3 and the fourth microfluidic channel 4 that intersect at the second intersection 11 are at right angles.

Having right angles at the first intersection 10 and at the second intersection 11 enable an easiest separation of the precursor water-absorbing polymer particles coated with the first coating solution and of the coated water-absorbing polymer particles.

Alternatively, first microfluidic channel 1 and the second microfluidic channel 2 that intersect at the first intersection 10 and the third microfluidic channel 3 and the fourth microfluidic channel 4 that intersect at the second intersection 11 may be not at right angles.

The microfluidic device 100 may comprise more than one part of the second microfluidic channel and more than one part of the fourth microfluidic channel. For example, each part of the second microfluidic channel may be located on each side of the microfluidic device 100 and may be connected at the first intersection 10. Each part of the second microfluidic channel may be linear.

The connected microfluidic channels on each side of the first intersection 10 may avoid unacceptable collisions of the precursor water-absorbing polymer particles with the wall of the microfluidic channel. The frictional force between the precursor water-absorbing polymer particles and the wall of the microfluidic channel may be reduced.

The same may apply for the connected microfluidic channels on each side of each intersections of the microfluidic device 100.

In addition, each part of the fourth microfluidic channel may be located on each side of the microfluidic device 100 and may be connected at the second intersection 11. Each part of the fourth microfluidic channel may be linear.

Preferably, the first intersection 10 between the first microfluidic channel 1 and the second microfluidic channel 2 are a T-junction arrangement, a X-junction arrangement or a co-flow junction in which the first microfluidic channel 1 and the second microfluidic channel 2 are disposed relative to each other such that the precursor water-absorbing polymer particles and the first coating solution flow toward the first intersection in the same direction.

Preferably, the second intersection 11 between the third microfluidic channel 3 and the fourth microfluidic channel 4 are a T-junction arrangement, a X-junction arrangement or a co-flow junction in which the third microfluidic channel 3 and the fourth microfluidic channel 4 are disposed relative to each other such that the coated water-absorbing polymer particles and the first non aqueous liquid flow toward the first intersection in the same direction.

The microfluidic device 100 may comprise other intersections that have the same arrangement as disclosed above.

The microfluidic device 100 may comprise a funnel 30 attached to the first microfluidic channel 1. The funnel 30 may collect the precursor water-absorbing polymer particles before the precursor water-absorbing polymer particles flow through the first microfluidic channel 1 toward the first intersection 10.

The microfluidic device 100 allows a continuous flow of different liquids or particles through micro channels. The liquid flow may be achieved by external pressure sources, external mechanical pumps, integrated mechanical micropumps or combinations of capillary forces and electric kinetic mechanisms. The flow of liquids in the microfluidic device 100 may be continuous or intermittent flow. Preferably, the surface-coated water-absorbing polymer particles are formed by delivering a pulsating flow of precursor water-absorbing polymer particles from the first microfluidic channel 1 into the first intersection 10. This has the advantage to enable the precursor water-absorbing polymer particles to flow through the first microfluidic channel 1.

A pulsating flow of the first coating solution may also be implemented on the second microfluidic channel 2. A pulsating flow of the non aqueous liquid may also be implemented on the fourth microfluidic channel 4.

Typically, the diameter of the microfluidic channels in the microfluidic device 100 is from 10 µm to 5000 µm, preferably from 30 µm to 3500 µm, more preferably from 100 µm to 2000 µm. The diameter of the microfluidic channels may be smaller than the diameter of the precursor water-absorbing polymer particles in order to have a regular pulsating flow of precursor water-absorbing polymer particles through the first microfluidic channel 1.

The microfluidic channels of the microfluidic device 100, i.e. the first microfluidic channel 1, the second microfluidic channel 2 and the third microfluidic channel 3 may be made of any suitable material conventionally used for this purpose. For example, the material of the microfluidic channels in the microfluidic device 100 may be metal, glass, polydimethylsiloxane (PDMS), polymethylmethacrylate (PMMA), cyclic olefin copolymers (COC), tetrafluoroethylenehexafluoropropylene copolymer (FEP) or polytetrafluoroethylene (PTFE). Preferably, the inner surfaces of the microfluidic channels present a surface of a material having a low coefficient of friction or other nonstick surface.

The flow rate of the precursor water-absorbing polymer particles, of the first coating solution, of the first non aqueous liquid and of the precursor water-absorbing polymer particles coated with the first coating solution through the respective microfluidic channels may depend on the inner diameter of the microfluidic channels and on the desired rate at which the surface-coated water-absorbing polymer particles should be formed. The desired flow rate of the precursor water-absorbing polymer particles, of the first coating solution, of the first non aqueous liquid and of the precursor water-absorbing polymer particles coated with the first coating solution through the respective microfluidic channels may be from 0.5 to 10 mL/min, preferably from 1 to 5 mL/min, more preferably from 2 to 4 mL/min.

Preferably, the direction of flow is in a downward direction and the precursor water-absorbing polymer particles fall gradually and independently through the first coating solution and through the first non aqueous liquid.

The flow of the first coating solution may not damage the individual integrity of the precursor water-absorbing polymer particles which are falling through the first microfluidic channel 1 toward the first intersection 10. Therefore, the flow should be sufficiently non-turbulent that it does not lead to unacceptable collisions of the precursor water-absorbing polymer particles especially while they are falling through the first microfluidic channel 1. Moreover, the flow should be sufficiently non-disruptive that it does not cause shearing the particles while they are flowing down. Preferably, the flow of the first coating solution is substantially a laminar flow.

In addition, the flow of the first non aqueous liquid may also not disrupt the individual integrity of the precursor water-absorbing polymer particles coated with the first coating solution which are falling through the third microfluidic channel 3 toward the second intersection 11.

However, a small amount of the flow of the first coating solution and the flow of the first non aqueous liquid may be a non-laminar flow with the consequential formation of swirls or eddies.

The microfluidic device 100 may comprise a fifth microfluidic channel 5 conveying the surface-coated water-absorbing polymer particles. The second intersection 11 may be in communication with the fifth microfluidic channel 5. The step of polymerization or the step of crosslinking may take place at the second intersection 11 or after the second intersection 11, in the fifth microfluidic channel 5 of the microfluidic device 100.

The microfluidic device may comprise a plurality of other microfluidic channels and of intersection that are not represented on FIG. 1.

The microfluidic device may be adjacent to a vessel (not represented on FIG. 1). The vessel may collect the particles that are formed by the microfluidic device. In particular, the vessel may collect the surface-coated water-absorbing polymer particles formed by the microfluidic device 100.

Method of Making Surface-Coated Water-Absorbing Polymer Particles in a Microfluidic Device The method of making surface-coated water-absorbing polymer particles in a microfluidic device comprises the steps of:

a) providing precursor water-absorbing polymer particles, the first coating solution and the first non aqueous liquid, b) feeding the precursor water-absorbing polymer particles in the first microfluidic channel 1 of the microfluidic device 100, c) feeding the first coating solution in the second microfluidic channel 2 of the microfluidic device 100, d) feeding the first non aqueous liquid in the fourth microfluidic channel 4 of the microfluidic device 100, e) coating precursor water-absorbing polymer particles with the first coating solution at the first intersection and/or in the third microfluidic channel, f) conveying the precursor water-absorbing polymer particles coated with the first coating solution through the third microfluidic channel toward the second intersection, g) separating the precursor water-absorbing polymer particles coated with the first coating solution from each other with the first non aqueous liquid at the second intersection 11, and, h) polymerizing the coated water-absorbing polymer particles to obtain surface-coated water-absorbing polymer particles, or i) crosslinking the coated water-absorbing polymer particles to obtain surface-coated water-absorbing polymer particles.

After the formation of the precursor water-absorbing polymer particles, they may be collected in a container prior to the step b) disclosed above.

The precursor water-absorbing polymer particles may be poured in a funnel attached to the first microfluidic channel 1 before going through the first microfluidic channel 1.

The precursor water-absorbing polymer particles may be naked precursor water-absorbing polymer particles or a dispersion of precursor water-absorbing polymer particles in a carrier liquid. Preferably, the precursor water-absorbing polymer particles are dispersed in a carrier liquid.

Having precursor water-absorbing polymer particles that are naked lead to an agglomeration of the particles when they are collected in a container before being fed in the microfluidic device 100. Moreover, the naked precursor water-absorbing polymer particles can also form an agglomeration of particles in a funnel attached to the first microfluidic channel 1 blocking the flow of particles through the first microfluidic channel 1. Therefore, there is a need to bring the particles in a single unit of particles in order to improve the coating of the precursor water-absorbing polymer particles by the first coating solution. Thus, it is preferred to have precursor water-absorbing polymer particles in a carrier liquid.

The carrier liquid may be the first non aqueous liquid or a second non aqueous liquid. The second non aqueous liquid may be a mixture of non-aqueous liquid and surfactants. The second non aqueous liquid may be selected from the group consisting of hydrocarbon oil, liquid fatty alcohol, fluorinated oil and silicone oil. The surfactants may be selected from the group consisting of amphiphilic surfactants with perfluoropolyether chains or perfluoroalkyl chains and hydrophilic head groups.

The second non aqueous liquid may be different from the first non aqueous liquid. The amount of carrier liquid present in the dispersion of precursor water-absorbing polymer particles may be from 10% to 30% by weight compared to the total weight of the precursor water-absorbing polymer particles.

For example, the precursor water-absorbing polymer particles may be dispersed in a minimum amount of a mixture of oil and surfactant.

Having precursor water-absorbing polymer particles in a carrier liquid such as a mixture of oil and surfactants, may avoid the agglomeration of particles in a funnel of the microfluidic device where the particles are collected. The rate flow of the precursor water-absorbing polymer particles may be higher through the first microfluidic channel 1 compared to the rate flow of the naked precursor water-absorbing polymer particles. The flow of precursor water-absorbing polymer particles may form an individualized flow of particles that enables each precursor water-absorbing polymer particle to be coated with the first coating solution.

Furthermore, having precursor water-absorbing polymer particles in a carrier liquid such as a mixture of oil and surfactants, may create particles with a low degree of neutralization and with a low ionic strength. Due to the fact that the first coating solution has a relatively high degree of neutralization, the coating of the precursor water-absorbing polymer particles with the first coating solution may equilibrates the degree of neutralization of the coated water-absorbing polymer particles obtained. Thus, the coated water-absorbing polymer particles may have a medium degree of neutralization.

In step e) of the process described above, at the first intersection 10 and/or in the third microfluidic channel 3, the precursor water-absorbing polymer particles are coated with the first coating solution. As the precursor water-absorbing polymer particles may form an individualized flow of particles, each single precursor water-absorbing polymer particles may be coated with the first coating solution in order to form coated water-absorbing polymer particles.

Alternatively, it may happen that drops of the first coating solution, i.e. particles that do not contain precursor water-absorbing polymer particles may be obtained at the first intersection 10 and/or in the third microfluidic channel 3.

Alternatively, two precursor water-absorbing polymer particles may be coated together with the first coating solution. Two "core" precursor water-absorbing polymer particles surrounded by the first coating solution may be obtained. However, obtaining drops of only the first coating solution and/or two "core" precursor water-absorbing polymer particles surrounded by the first coating solution are not desirable. In order to avoid having this kind of undesirable materials, the flow rates of the first coating solution and of the first non aqueous liquid are controlled and adjusted.

The precursor water-absorbing polymer particles coated with the first coating solution obtained at the first intersection 10 and/or in the third microfluidic channel 3 correspond to precursor water-absorbing polymer particles coated with an aqueous solution.

With the use of the microfluidic device 100 with microfluidic channels, the aqueous polymerization solution is distributed around the surface of the precursor water-absorbing polymer particles in order to form spherical precursor water-absorbing polymer particles coated with the first coating solution.

The first coating solution forms a shell around each precursor water-absorbing polymer particles.

In step f) of the process above, the precursor water-absorbing polymer particles coated with the first coating solution are conveyed through the third microfluidic channel 3 toward the second intersection 11, In step g) of the process described above, the precursor water-absorbing polymer particles coated with the first coating solution are separated from each other with the first non aqueous liquid at the second intersection 11.

The first non aqueous liquid flows through the fourth microfluidic channel 4 toward the second intersection 11. The precursor water-absorbing polymer particles coated with the first coating solution flow through the third microfluidic channel 3 toward the second intersection 11. The first non aqueous liquid contacts the precursor water-absorbing polymer particles coated with the first coating solution at the second intersection 11 and separate the precursor water-absorbing polymer particles coated with the first coating solution from one another.

The first non aqueous liquid may cover entirely the surface of the precursor water-absorbing polymer particles coated with the first coating solution.

The first non aqueous liquid and the first coating solution distributed on the surface of the coated water-absorbing polymer particles may be non miscible. Therefore, the two liquids may not mix together. The first non aqueous liquid may not migrate through the first coating solution onto the "core" particles, i.e. precursor water-absorbing polymer particles.

Alternatively, it may happen that instead of a single coated water-absorbing polymer particle to be separated with the first non aqueous liquid, drops of only the first coating solution and/or two "core" precursor water-absorbing polymer particles surrounded by the first coating solution may be separated by the first non aqueous liquid. However, these particles may not be desirable.

In step h) of the process described above, the step of polymerization may take place at the second intersection 11 or after the second intersection 11.

Preferably, the step of polymerization takes place at the second intersection 11 or in the fifth microfluidic channel 5 of the microfluidic device 100.

The process of the present invention may employ any of the conventional polymerization techniques, such as redox initiated polymerization, photo polymerization or thermal polymerization or combination of two or more initiation techniques.

A preferred polymerization technique employs electromagnetic radiation or actinic radiation in combination with polymerization initiator system added to the first coating solution. More preferably, the polymerization technique employs ultraviolet radiation in combination with suitable UV photo initiators as polymerization initiator system. The ultraviolet light source may be any conventional ultraviolet light source conventionally used in UV polymerization technique. For example, the ultraviolet light source may be a light source comprising a light emitting diode (LED), for instance an LED array.

The polymerization technique may be applied at the second intersection 11 or after the second intersection 11, i.e on the fifth microfluidic channel 5 of the microfluidic device 100.

The wall of the second intersection and/or of the fifth microfluidic channel may comprise a transparent portion and the light source may be mounted externally such that the UV radiation from the light source can penetrate the wall of the second intersection 11 and/or of the fifth microfluidic channel 5. Suitable light source may be in communication with an external surface of the transparent portion of the second intersection 11 and/or of the fifth microfluidic channel 5. The light source may be positioned on each side of the fifth microfluidic channel 5 such that the fifth microfluidic channel is surrounded by the light source. More than one light source may be used.

Preferably, the light source is mounted at a distance of up to 10 cm, more preferably within 0.1 to 5.0 cm from the external surface of the transparent portion of the second intersection 11 and/or of the fifth microfluidic channel 5.

The transparent portion of the second intersection 11 and/or of the fifth microfluidic channel 5 may be formed from a suitable material which is substantially transparent to UV light. For instance, the material of the transparent portion may be glass such as quartz glass or borosilicate glass, or plastic.

The time required for the coated water-absorbing polymer particles to polymerize sufficiently that they become solid depend on the choice of the polymerization initiator system and on the polymerization conditions in the microfluidic device 100.

The coated water-absorbing polymer particles are polymerized to obtain surface-coated water-absorbing polymer particles.

Alternatively, in step i) of the process described above, the step of crosslinking may take place at the second intersection 11 or after the second intersection 11.

Preferably, the step of crosslinking takes place at the second intersection 11 or in the fifth microfluidic channel 5 of the microfluidic device 100.

The process of the present invention may employ any of the conventional crosslinking techniques, such as thermal reaction or ultraviolet radiation. For example, the crosslinking step may be a heating step at a temperature of 120° C. or higher than 120° C. or a drying step.

The wall of the second intersection and/or of the fifth microfluidic channel may comprise a transparent portion and the light source may be mounted externally such that the ultraviolet radiation from the light source can penetrate the wall of the second intersection 11 and/or of the fifth microfluidic channel 5.

Alternatively, it may happen that the precursor water-absorbing polymer particles without any coating of the first coating solution may be polymerized or crosslinked or that two "core" precursor water-absorbing polymer particles surrounded by the first coating solution may also be polymerized or crosslinked.

Alternatively, drops of only the first coating solution may be polymerized.

After step h) or i) of the process described above, the surface-coated water-absorbing polymer particles may be collected in a vessel.

The surface-coated water-absorbing polymer particles collected in the vessel may be placed again in the microfluidic device for a second coating step or may be placed in another device. The surface-coated water-absorbing polymer particles may be coated again with the first coating solution or with a second coating solution. The second coating solution may comprise particles such as inorganic solids and either polymerizable monomers and/or oligomers, or crosslinkable polymers.

The second coating solution may be different from the first coating solution.

Alternatively, after step h) or i) of the process described above, the surface-coated water-absorbing polymer particles may be conveyed through the fifth microfluidic channel 5 toward a third intersection (not represented on FIG. 1).

Then, the surface-coated water-absorbing polymer particles may be coated again with the first coating solution or with the second coating solution at the third intersection and/or in a sixth microfluidic channel of the microfluidic device 100 (not represented on FIG. 1).

In this specific embodiment, the first coating solution or the second coating solution may be conveyed in a seventh microfluidic channel of the microfluidic device 100 (not represented on FIG. 1). The third intersection may be in communication with the fifth microfluidic channel, with the sixth microfluidic channel and with the seventh microfluidic channel.

A second step of polymerization or a second step of crosslinking may take place after the second step of coating the surface-coated water-absorbing polymer particles. The second step of polymerization or the second step of crosslinking is similar to the step of polymerization described above.

The precursor water-absorbing polymer particles may be coated with one or more coating solution in one or more microfluidic device.

The precursor water-absorbing polymer particles may only be coated once.

The method described above may also comprise a further step after step h) or i). The surface coated water absorbing polymer particles may be treated with a surface treatment such as a surface cross-linking. The cross-linking step corresponds to the step of post-crosslinking explained above.

Absorbent Articles

A typical disposable absorbent article, in which the surface-coated water-absorbing polymer particles of the present invention can be used, is placed against or in proximity to the body of the wearer to absorb and contain the various exudates discharged from the body and is represented in FIG. 2 to FIG. 6 in the form of a diaper 20.

Figure 2:
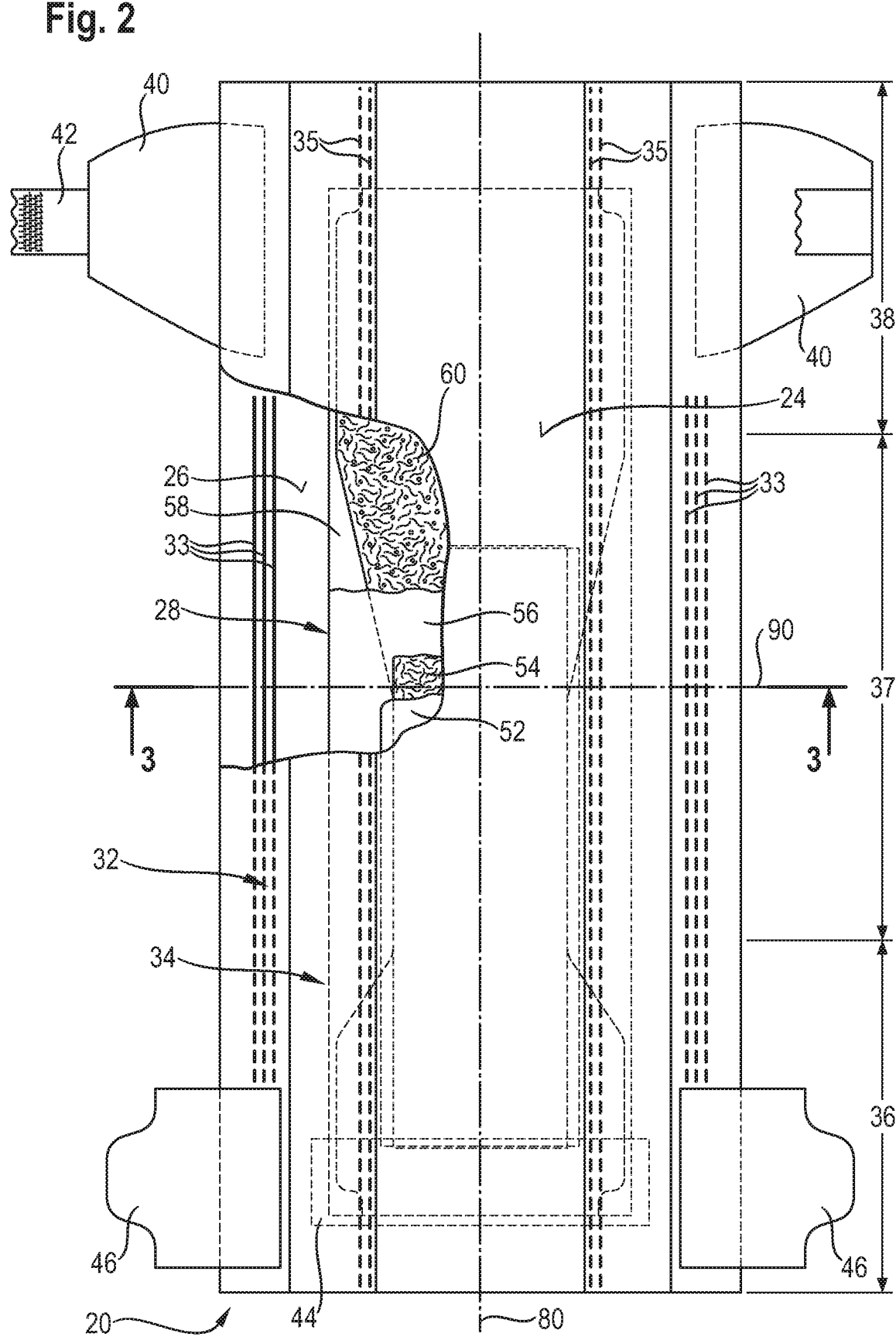
FIG. 2 is a top view of an exemplary absorbent article in the form of a diaper, which may comprise the water-absorbing polymer particles of the present invention, with some layers partially removed.

In more details, FIG. 2 is a plan view of an exemplary diaper 20, in a flat-out state, with portions of the diaper being cut-away to more clearly show the construction of the diaper 20. This diaper 20 is shown for illustration purpose only as the structure of the present invention may be comprised in a wide variety of diapers or other absorbent articles.

Figure 3:
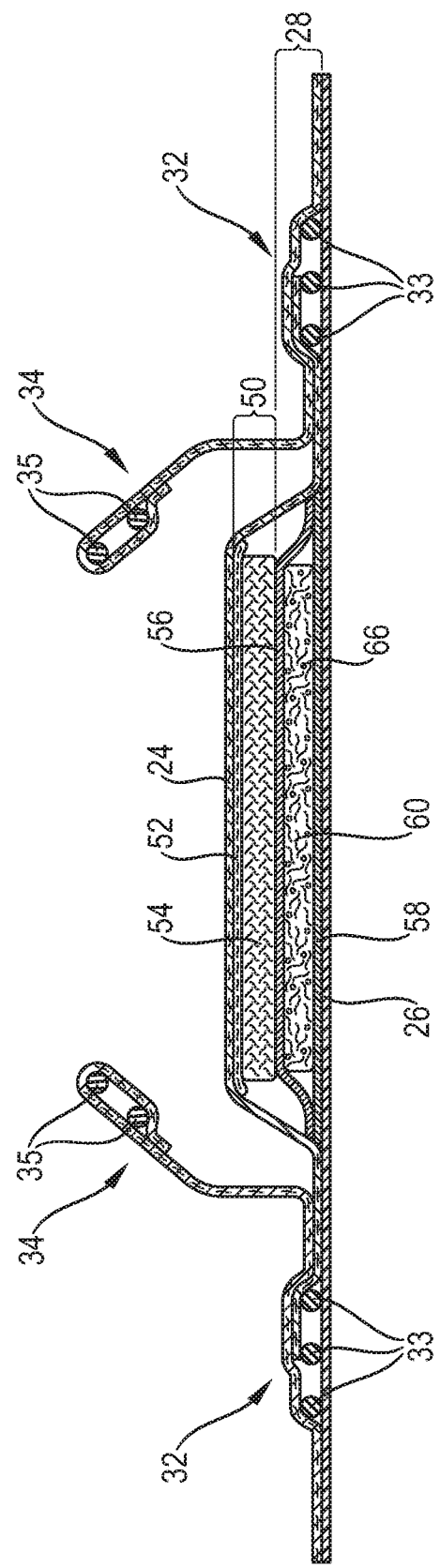
FIG. 3 is a transversal cross-section of the diaper of FIG. 2.

As shown in FIGS. 2 and 3, the absorbent article, here a diaper, can comprise a liquid pervious topsheet 24, a liquid impervious backsheet 26, an absorbent core 28 which is positioned between the topsheet 24 and the backsheet 26. The absorbent core 28 can absorb and contain liquid received by the absorbent article and may comprise absorbent materials 60, such as the water-absorbing polymer particles of the present invention 66 and/or cellulose fibers, as well as other absorbent and non-absorbent materials commonly used in absorbent articles (e.g. thermoplastic adhesives immobilizing the water-absorbing polymer particles). The absorbent material and non-absorbent material may be wrapped within a substrate (e.g. one or more nonwovens, tissues etc.) such as by an upper core cover layer 56 facing towards the topsheet and a lower cover layer 58 facing towards the backsheet. Such upper and lower core cover layers may be made of nonwovens, tissues or the like and may be attached to each other continuously or discontinuously, e.g. along their perimeter The absorbent core may comprise one or more substrate layer(s) (such as nonwoven webs or paper tissue), water-absorbing polymer particles disposed on the one or more substrate layers, and a thermoplastic composition typically disposed on the water-absorbing polymer particles. Typically the thermoplastic composition is a thermoplastic adhesive material. In one embodiment, the thermoplastic adhesive material forms a fibrous layer which is at least partially in contact with the water-absorbing polymer particles on the one or more substrate layers and partially in contact with the one or more substrate layers. Auxiliary adhesive might be deposited on the one or more substrate layers before application of the water-absorbing polymer particles for enhancing adhesion of the water-absorbing polymer particles and/ or of the thermoplastic adhesive material to the respective substrate layer(s). The absorbent core may also include one or more cover layer(s) such that the water-absorbing polymer particles are comprised between the one or more substrate layer(s) and the one or more cover layer(s). The one or more substrate layer(s) and the cover layer(s) may comprise or consist of a nonwoven web. The absorbent core may further comprise odor control compounds.

The absorbent core may consist essentially of the one or more substrate layer(s), the water-absorbing polymer particles, the thermoplastic composition, optionally the auxiliary adhesive, optionally the cover layer(s), and optionally odor control compounds.

The absorbent core may also comprise a mixture of water-absorbing polymer particles and airfelt, which may be enwrapped within one or more substrate layers, such as nonwoven webs or paper tissue. Such absorbent cores may comprise from 30% to 95%, or from 50% to 95% of water-absorbing polymer particles by weight of the absorbent material and may comprise from 5% to 70%, or from 5% to 50% of airfelt by weight of the absorbent material (for these percentages, any enwrapping substrate layers are not considered as absorbent material). The absorbent core may also be free of airfelt and may comprise 100% of water-absorbing polymer particles by weight of the absorbent material.

The absorbent core may comprise mixtures of the water-absorbing polymer particles of the present invention and other water-absorbing polymer particles. For example, the absorbent core may comprise at least 70%, or at least 80%, or at least 90% or 100% of water-absorbing polymer particles by weight of the absorbent material, wherein the water-absorbing polymer particles comprise at least 10%, or at least 20% or at least 30% or at least 50% by weight of the water-absorbing polymer particles.

The absorbent articles of the invention, especially diapers and pants, may comprise an acquisition layer 52, a distribution layer 54, or combination of both (all herein collectively referred to as acquisition-distribution system "ADS" 50). The function of the ADS 50 is typically to quickly acquire the fluid and distribute it to the absorbent core in an efficient manner. The ADS may comprise one, two or more layers.

The ADS may be free of water-absorbing polymer particles. The prior art discloses many types of acquisition-distribution systems, see for example WO2000/59430, WO95/10996, U.S. Pat. No. 5,700,254, WO02/067809. However, the water-absorbing polymer particles of the present invention may also be comprised by the ADS.

The function of a distribution layer 54 is to spread the insulting fluid liquid over a larger surface within the article so that the absorbent capacity of the absorbent core can be more efficiently used. Distribution layers may be made of a nonwoven material based on synthetic or cellulosic fibers and having a relatively low density. The distribution layer may typically have an average basis weight of from 30 to 400 g/m$^2$, in particular from 80 to 300 g/m$^2$.

The distribution layer may for example comprise at least 50%, or 60%, or 70%, or 80%, or 90% by weight of cross-linked cellulose fibers. The cross-linked cellulosic fibers may be crimped, twisted, or curled, or a combination thereof including crimped, twisted, and curled. The cross-linked cellulosic fibers provide higher resilience and therefore higher resistance to the first absorbent layer against the compression in the product packaging or in use conditions, e.g. under baby weight. This provides the core with a relatively high void volume, permeability and liquid absorption, and hence reduced leakage and improved dryness.

The distribution layer comprising cross-linked cellulose fibers, may comprise other fibers, but this layer may advantageously comprise at least 50%, or 60%, or 70%, or 80%, or 90% or even up to 100%, by weight of the layer, of cross-linked cellulose fibers. Examples of such mixed layer of cross-linked cellulose fibers may comprise 70% by weight of chemically cross-linked cellulose fibers, 10% by weight polyester (PET) fibers, and 20% by weight untreated pulp fibers. In another example, the layer of cross-linked cellulose fibers may comprise 70% by weight chemically cross-linked cellulose fibers, 20% by weight lyocell fibers, and 10% by weight PET fibers. In another example, the layer may comprise 68% by weight chemically cross-linked cellulose fibers, 16% by weight untreated pulp fibers, and 16% by weight PET fibers.

The absorbent article 20 may further comprise an acquisition layer 52, whose function is to quickly acquire the fluid away from the topsheet so as to provide a good dryness for the wearer. The acquisition layer 52 is typically placed directly under the topsheet and below the distribution layer. The acquisition layer may typically be or comprise a nonwoven material, for example a SMS or SMMS material, comprising a spunbonded, a melt-blown and a further spunbonded layer or alternatively a carded chemical-bonded nonwoven. The non-woven material may in particular be latex bonded. Exemplary upper acquisition layers 52 are disclosed in U.S. Pat. No. 7,786,341. Carded, resin-bonded nonwovens may be used, in particular where the fibers used are solid round or round and hollow PET staple fibers (such as a 50/50 or 40/60 mix of 6 denier and 9 denier fibers). An exemplary binder is a butadiene/styrene latex.

The acquisition layer 52 may be stabilized by a latex binder, for example a styrene-butadiene latex binder (SB latex). Processes for obtaining such lattices are known, for example, from EP 149 880 (Kwok) and US 2003/0105190 (Diehl et al.). The binder may be present in the acquisition layer 52 in excess of 12%, 14% or 16% by weight, but may be present by not more than 30%, or not more than 25% by weight of the acquisition layer. SB latex is available under the trade name GENFLO™ 3160 (OMNOVA Solutions Inc.; Akron, Ohio).

A further acquisition layer may be used in addition to a first acquisition layer described above. For example a tissue layer may be placed between the first acquisition layer and the distribution layer. The tissue may have enhanced capillarity distribution properties compared to the acquisition layer described above. The tissue and the first acquisition layer may be of the same size or may be of different size, for example the tissue layer may extend further in the back of the absorbent article than the first acquisition layer. An example of hydrophilic tissue is a 13 to 15 gsm high wet strength made of cellulose fibers from supplier Havix.

The diaper may also comprise elasticized leg cuffs 32 and barrier leg cuffs 34, which provide improved containment of liquids and other body exudates especially in the area of the leg openings. Usually each leg cuffs 32 and barrier cuffs 34 will comprise one or more elastic string 33 and 35, represented in exaggerated form on FIGS. 2 and 3. Moreover, the diaper 20 may comprise other features such as back ears 40, front ears 46 and/or barrier cuffs 34 attached to form the composite diaper structure. The diaper may further comprise a fastening system, such as an adhesive fastening system or a mechanical fastening system (e.g. a hook and loop fastening system), which can comprise tape tabs 42, such as adhesive tape tabs or tape tabs comprising hook elements, cooperating with a landing zone 44 (e.g. a nonwoven web providing loops in a hook and loop fastening system). Further, the diaper may comprise other elements, such as a back elastic waist feature and a front elastic waist feature, side panels or a lotion application.

The diaper 20 as shown in FIGS. 2 and 3 can be notionally divided in a first waist region 36, a second waist region 38 opposed to the first waist region 36 and a crotch region 37 located between the first waist region 36 and the second waist region 38. The longitudinal centerline 80 is the imaginary line separating the diaper along its length in two equal halves. The transversal centerline 90 is the imagery line perpendicular to the longitudinal line 80 in the plane of the flattened out diaper and going through the middle of the length of the diaper. The periphery of the diaper 20 is defined by the outer edges of the diaper 20. The longitudinal edges of the diaper may run generally parallel to the longitudinal centerline 80 of the diaper 20 and the end edges run between the longitudinal edges generally parallel to the transversal centerline 90 of the diaper 20.

Area(s) 29 substantially free of absorbent material and channels 29'

Figure 4:
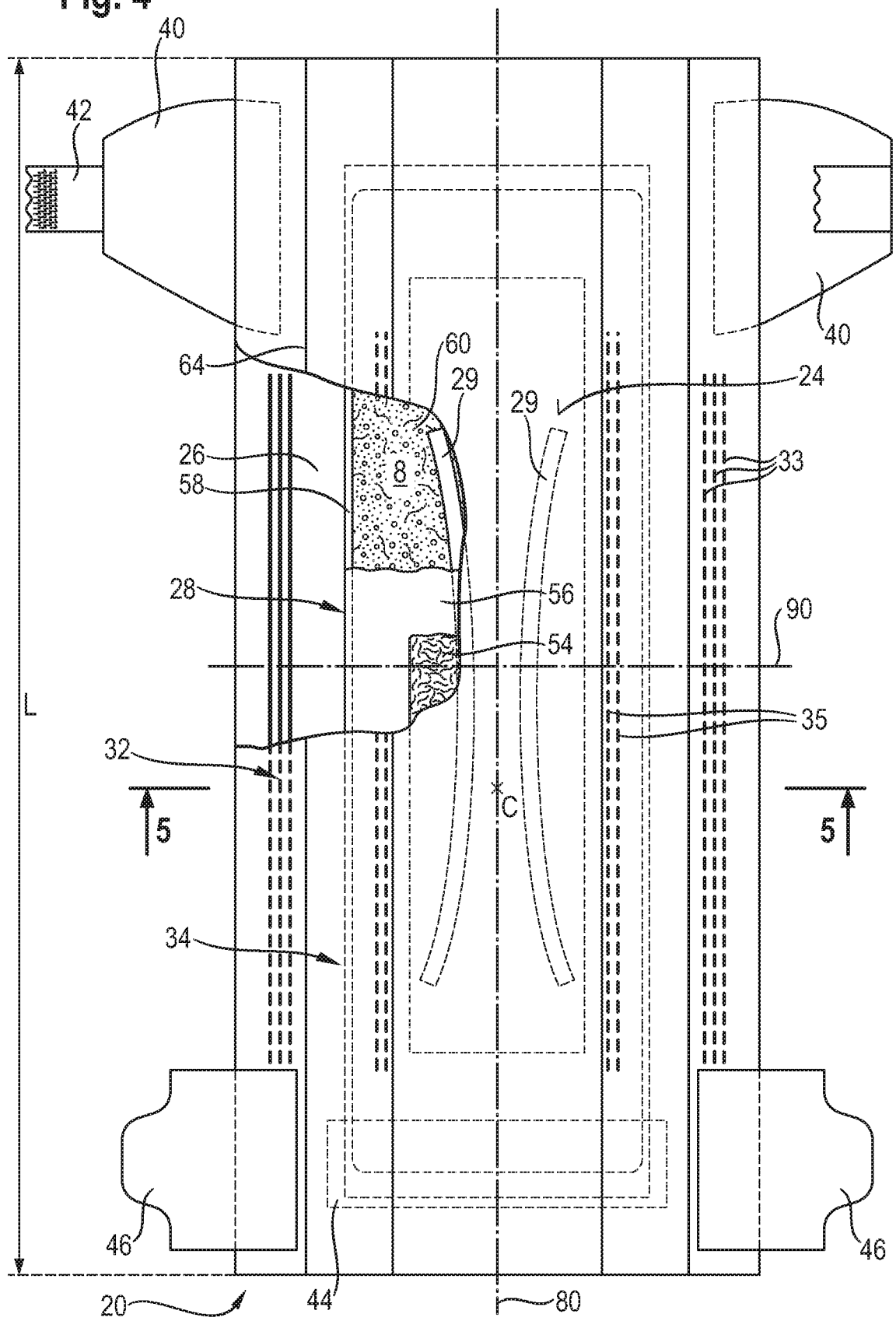
FIG. 4 is a top view of an exemplary absorbent article in the form of a diaper which may comprise the water-absorbing polymer particles of the present invention, with area(s) substantially free of absorbent material.

As shown in FIG. 4, the absorbent core 28 may comprise one or more area(s) 29 which is/are substantially free of absorbent material. By "substantially free" it is meant that in each of these areas the basis weight of the absorbent material is less than 25%, in particular less than 20%, less than 10%, of the average basis weight of the absorbent material in the rest of the core. In particular there can be no absorbent material in these areas. Minimal amount such as involuntary contaminations with absorbent material that may occur during the making process are not considered as absorbent material. The areas 29 are advantageously surrounded by the absorbent material, when seen in the plane of the core, which means that the area(s) 29 does not extend to any of the edge of the deposition area 8 of the absorbent material.

Figure 5:
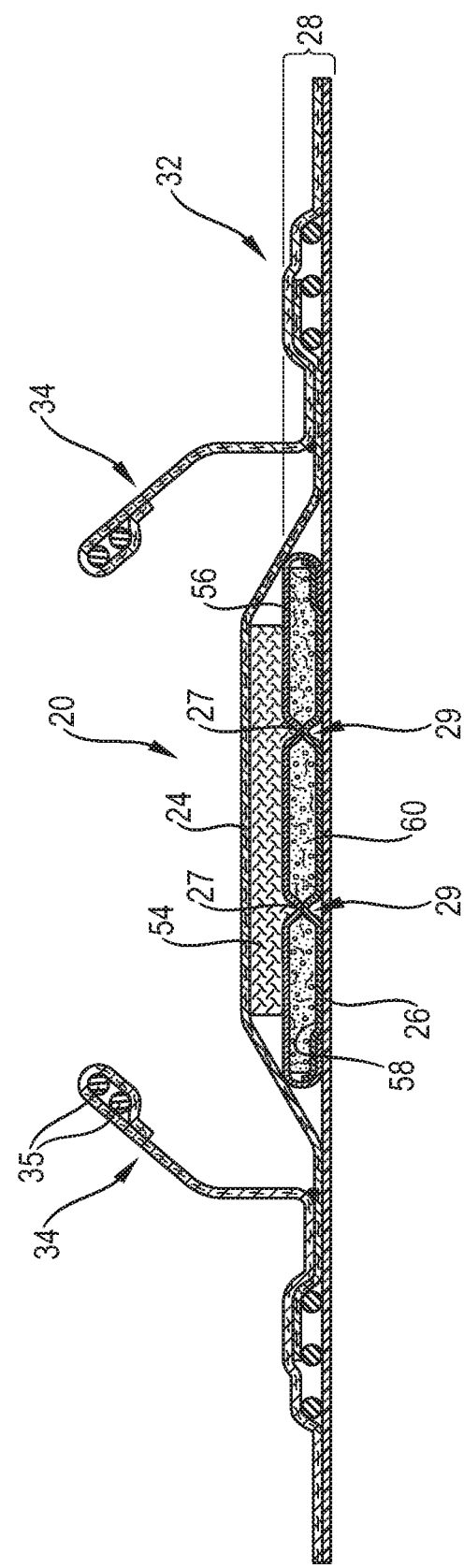
FIG. 5 is a transversal cross-section of the article of FIG. 4.
Figure 6:
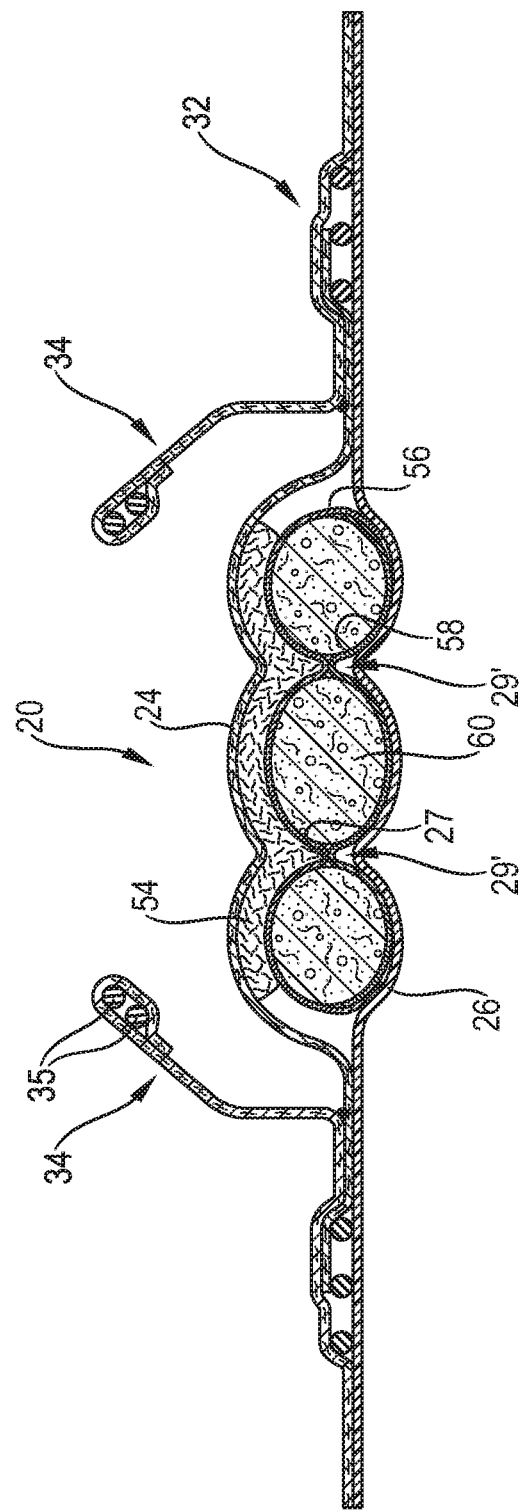
FIG. 6 is a transversal cross-section of the article taken at the same point as FIG. 5 where channels have formed in the core as a result of the diaper being loaded with fluid.

The upper core cover layer 56 is attached to the lower cover layer 58 by core wrap bond(s) 27 through these area(s) 29 substantially free of absorbent material. As shown in FIG. 5 and FIG. 6, when the absorbent material swells upon absorbing a liquid, the core wrap bond remains at least initially attached in the substantially material free area(s) 29. The absorbent material swells in the rest of the core when it absorbs a liquid, so that the core wrap forms one or more channel(s) 29' along the area(s) 29 substantially free of absorbent material comprising the core wrap bond 27. These channels 29' are three dimensional and can serve to distribute an insulting fluid along their length to a wider area of the core. This may provide a quicker fluid acquisition speed and a better utilization of the absorbent capacity of the core. The channels 29' can also provide a deformation of an overlying layer such as a fibrous layer 54 and provide corresponding ditches 29 in the overlying layer. It is not excluded that the absorbent core may comprise other area(s) substantially free of absorbent material but without a core wrap bond, but these non-bonded areas will typically not form a channel when wet.

The upper core cover layer 56 and the lower cover layer 58 may be attached together continuously along the area(s) 29 substantially free of absorbent material, but the core wrap bond 27 may also be discontinuous (intermittent) such as series of point bonds. Typically, an adhesive can be used to attach the top side to the bottom of the core wrap, but it is possible to bond via other known attachment means, such as pressure bonding, ultrasonic bonding or heat bonding or combination thereof. The attachment of the top side and bottom side of the core wrap may be provided by one or more adhesive material, in particular one or more layers of auxiliary glue and/or one or more layers of fibrous adhesive material, if present in the core, as indicated below. These glues may therefore serve the dual function of immobilizing the absorbent material and attach the top side and the bottom side of the core together.

The following examples of the shape and size of the areas 29 substantially free of absorbent material are not limiting. In general, the core wrap bond 27 may have the same outline but be slightly smaller than the areas 29 due to the tolerance required in some manufacturing process. The substantially material free area(s) 29 may be present within the crotch region of the article, in particular at least at the same longitudinal level as the crotch point C, as represented in FIG. 4 by the two longitudinally extending areas substantially free of absorbent material 29. The absorbent core 28 may also comprise more than two substantially absorbent material free area(s), for example at least 3, or at least 4 or at least 5 or at least 6. The absorbent core may comprise one or more pairs of areas substantially free of absorbent material symmetrically arranged relative to the longitudinal axis 80. Shorter area(s) substantially free of absorbent material may also be present, for example in the back region or the front region of the core, as seen for example in the Figures of WO2012/170778.

The area(s) 29 substantially free of absorbent material may extend substantially longitudinally, which means typically that each area extends more in the longitudinal direction than in the transverse direction, and typically at least twice as much in the longitudinal direction than in the transverse direction (as measured after projection on the respective axis). The area(s) 29 substantially free of absorbent material may have a length projected on the longitudinal axis 80 of the core that is at least 10% of the length of the absorbent core, in particular from 20% to 80%. It may be advantageous that at least some or all of the area(s) 29 are not completely or substantially completely transversely oriented channels in the core.

The area(s) 29 substantially free of absorbent material may be completely oriented longitudinally and parallel to the longitudinal axis but also may be curved. In particular some or all these area(s), in particular these area(s) present in the crotch region, may be concave towards the longitudinal axis 80, as for example represented in FIG. 4 for the pair of channels 29'. The radius of curvature may typically be at least equal (and preferably at least 1.5 or at least 2.0 times this average transverse dimension) to the average transverse dimension of the absorbent material deposition area 8; and also straight but under an angle of (e.g. from 5°) up to 30°, or for example up to 20°, or up to 10° with a line parallel to the longitudinal axis. The radius of curvature may be constant for a substantially absorbent material free area(s), or may vary along its length. This may also includes area(s) substantially free of absorbent material with an angle therein, provided said angle between two parts of a channel is at least 120°, preferably at least 150°; and in any of these cases, provided the longitudinal extension of the area is more than the transverse extension. These area(s) may also be branched, for example a central substantially material free area superposed with the longitudinal axis in the crotch region which branches towards the back and/or towards the front of the article.

In some embodiments, there is no area(s) substantially free of absorbent material that coincides with the longitudinal axis 80 of the core. When present as one ore symmetrical pair(s) relative to the longitudinal axis, the area(s) substantially free of absorbent material may be spaced apart from one another over their whole longitudinal dimension. The smallest spacing distance may be for example at least 5 mm, or at least 10 mm, or at least 16 mm.

Furthermore, in order to reduce the risk of fluid leakages, the area(s) substantially free of absorbent material may advantageously not extend up to any of the edges of the absorbent material deposition area 8, and are therefore surrounded by and fully encompassed within the absorbent material deposition area 8 of the core. Typically, the smallest distance between an area(s) substantially free of absorbent material and the closest edge of the absorbent material deposition area is at least 5 mm.

The area(s) substantially free of absorbent material may have a width Wc along at least part of its length which is at least 2 mm, or at least 3 mm or at least 4 mm, up to for example 20 mm, or 16 mm or 12 mm. The width Wc of the area(s) substantially free of absorbent material may be constant through substantially its whole length or may vary along its length.

The channels 29' in the absorbent core start forming when the absorbent material absorbs a liquid such as urine and starts swelling. As the core absorbs more liquid, the depressions within the absorbent core formed by channels will become deeper and more apparent to the eye and the touch. It is possible to create a sufficiently strong core wrap bond combined with a relatively low amount of water-absorbing polymer particles so that the channels remain permanent until complete saturation of the absorbent material. On the other hand, the core wrap bonds may in some cases also restrict the swelling of the absorbent material when the core is substantially loaded.

Initially, the core wrap bond(s) may be designed to be closed and to increase the pressure in the areas adjacent to the core wrap bond(s). At some point, the core wrap bond 27 may also be designed to open in a controlled manner when exposed to a large amount of fluid.

Test Method:
Urine Permeability Measurement (UPM) Test Method
Lab Conditions:

This test has to be performed in a climate conditioned room at standard conditions of 23° C.±2° C. temperature and 45%±10% relative humidity.

Urine Permeability Measurement System

This method determined the permeability of a swollen hydrogel layer 1318. The equipment used for this method is described below. This method is closely related to the SFC (Salt Flow Conductivity or Saline Flow Conductivity) test method of the prior art.

Figure 7:
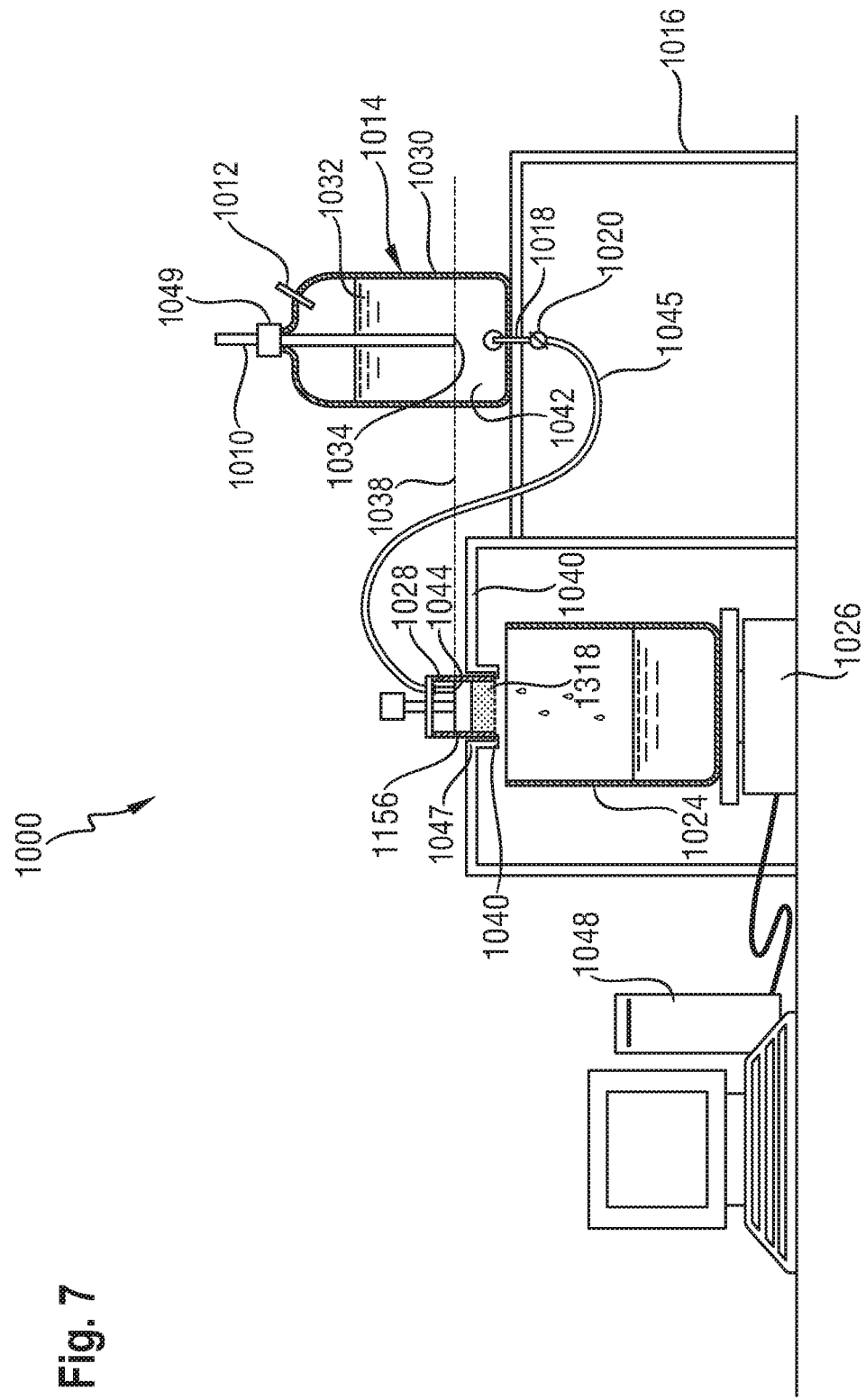
FIG. 7 is a partial cross-sectional side view of a suitable permeability measurement system for conducting the Urine Permeability Measurement Test.

FIG. 7 shows permeability measurement system 1000 set-up with the constant hydrostatic head reservoir 1014, open-ended tube for air admittance 1010, stoppered vent for refilling 1012, laboratory reck 1016, delivery tube 1018 with flexible tube 1045 with Tygon tube nozzle 1044, stopcock 1020, cover plate 1047 and supporting ring 1040, receiving vessel 1024, balance 1026 and piston/cylinder assembly 1028.

Figure 8:
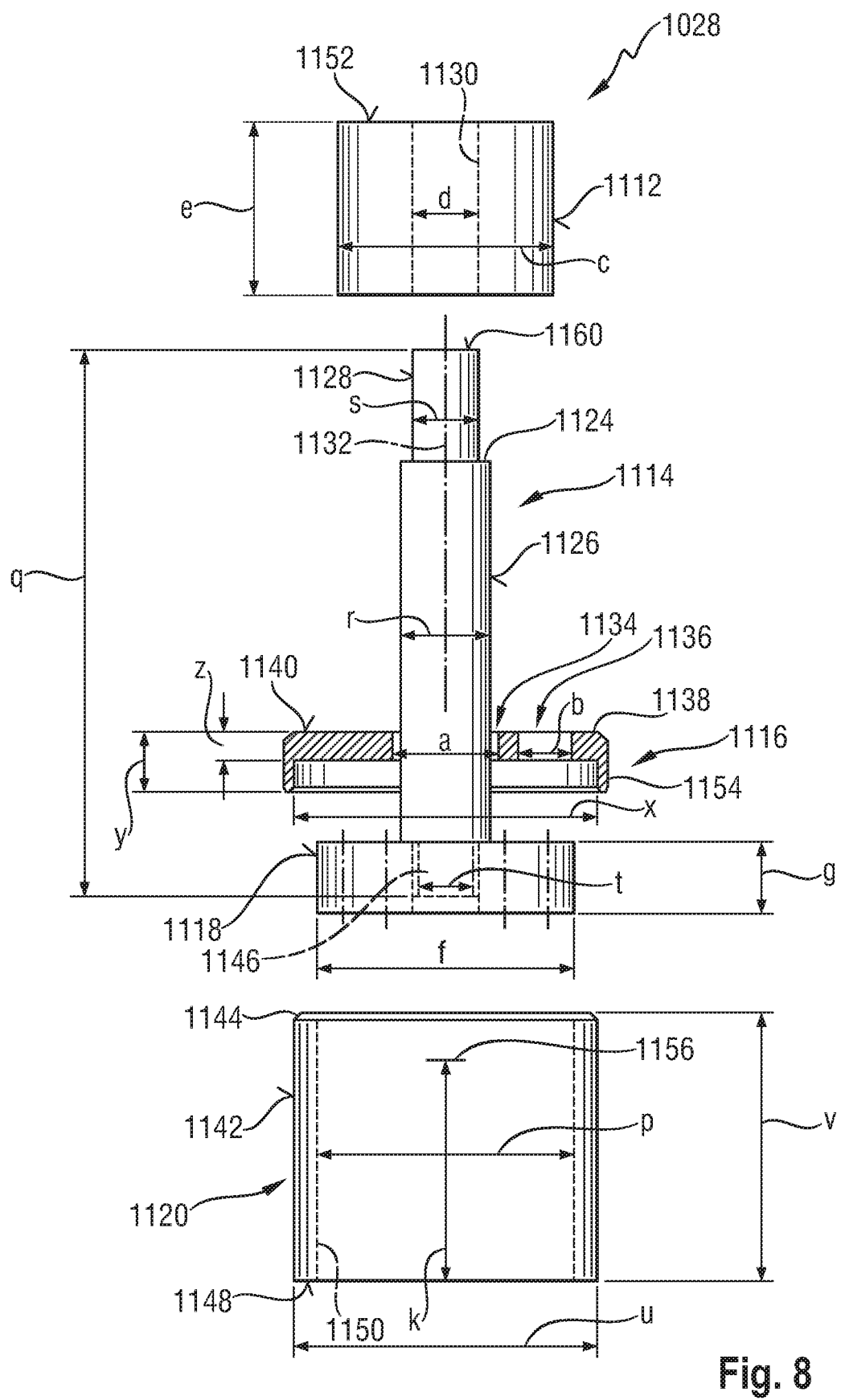
FIG. 8 is a cross-sectional side view of a piston/cylinder assembly for use in conducting the Urine Permeability Measurement Test.
Figure 9:
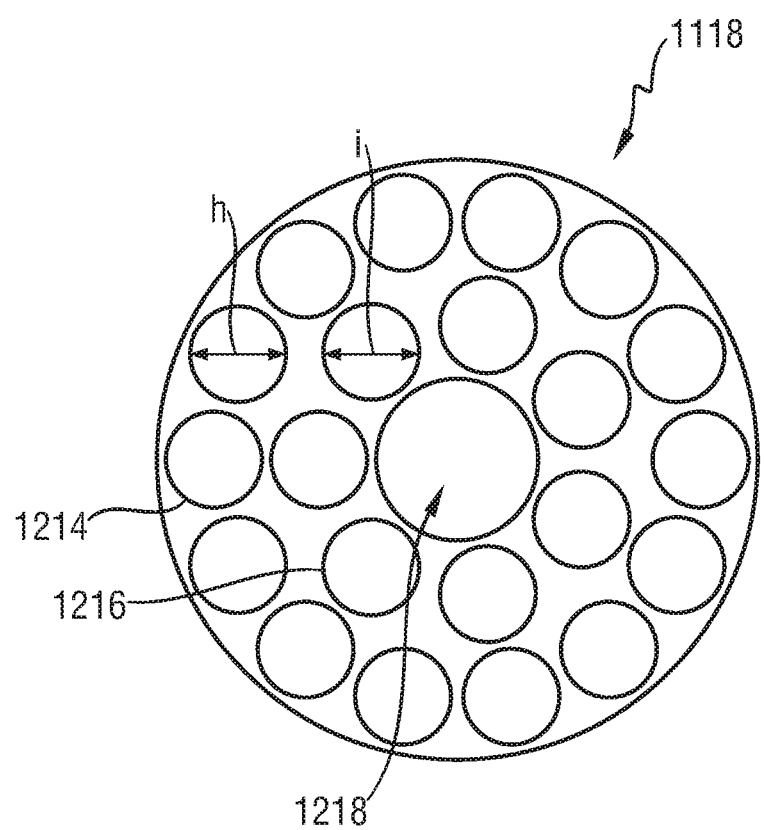
FIG. 9 is a top view of a piston head suitable for use in the piston/cylinder assembly shown in FIG. 8.

FIG. 8 shows the piston/cylinder assembly 1028 comprising a metal weight 1112, piston shaft 1114, piston head 1118, lid 1116, and cylinder 1120. The cylinder 1120 is made of transparent polycarbonate (e.g., Lexan®) and has an inner diameter p of 6.00 cm (area=28.27 cm$^2$) with inner cylinder walls 1150 which are smooth. The bottom 1148 of the cylinder 1120 is faced with a stainless-steel screen cloth (ISO 9044 Material 1.4401, mesh size 0.038 mm, wire diameter 0.025 mm) (not shown) that is bi-axially stretched to tautness prior to attachment to the bottom 1148 of the cylinder 1120. The piston shaft 1114 is made of transparent polycarbonate (e.g., Lexan®) and has an overall length q of approximately 127 mm. A middle portion 1126 of the piston shaft 1114 has a diameter r of 22.15 (±0.02) mm. An upper portion 1128 of the piston shaft 1114 has a diameters of 15.8 mm, forming a shoulder 1124. A lower portion 1146 of the piston shaft 1114 has a diameter t of approximately ⅝ inch (15.9 mm) and is threaded to screw firmly into the center hole 1218 (see FIG. 9) of the piston head 1118. The piston head 1118 is perforated, made of transparent polycarbonate (e.g., Lexan®), and is also screened with a stretched stainless-steel screen cloth (ISO 9044 Material 1.4401, mesh size 0.038 mm, wire diameter 0.025 mm) (not shown). The weight 1112 is stainless steel, has a center bore 1130, slides onto the upper portion 1128 of piston shaft 1114 and rests on the shoulder 1124. The combined weight of the piston head 1118, piston shaft 1114 and weight 1112 is 596 g (±6 g), which corresponds to 0.30 psi over the inner area of the cylinder 1120. The combined weight may be adjusted by drilling a blind hole down a central axis 1132 of the piston shaft 1114 to remove material and/or provide a cavity to add weight. The cylinder lid 1116 has a first lid opening 1134 in its center for vertically aligning the piston shaft 1114 and a second lid opening 1136 near the edge 1138 for introducing fluid from the constant hydrostatic head reservoir 1014 into the cylinder 1120.

A first linear index mark (not shown) is scribed radially along the upper surface 1152 of the weight 1112, the first linear index mark being transverse to the central axis 1132 of the piston shaft 1114. A corresponding second linear index mark (not shown) is scribed radially along the top surface 1160 of the piston shaft 1114, the second linear index mark being transverse to the central axis 1132 of the piston shaft 1114. A corresponding third linear index mark (not shown) is scribed along the middle portion 1126 of the piston shaft 1114, the third linear index mark being parallel with the central axis 1132 of the piston shaft 1114. A corresponding fourth linear index mark (not shown) is scribed radially along the upper surface 1140 of the cylinder lid 1116, the fourth linear index mark being transverse to the central axis 1132 of the piston shaft 1114. Further, a corresponding fifth linear index mark (not shown) is scribed along a lip 1154 of the cylinder lid 1116, the fifth linear index mark being parallel with the central axis 1132 of the piston shaft 1114. A corresponding sixth linear index mark (not shown) is scribed along the outer cylinder wall 1142, the sixth linear index mark being parallel with the central axis 1132 of the piston shaft 1114. Alignment of the first, second, third, fourth, fifth, and sixth linear index marks allows for the weight 1112, piston shaft 1114, cylinder lid 1116, and cylinder 1120 to be repositioned with the same orientation relative to one another for each measurement.

The cylinder 1120 specification details are:
Outer diameter u of the Cylinder 1120: 70.35 mm (±0.05 mm)
Inner diameter p of the Cylinder 1120: 60.0 mm (±0.05 mm)
Height v of the Cylinder 1120: 60.5 mm. Cylinder height must not be lower than 55.0 mm!
The cylinder lid 1116 specification details are:
Outer diameter w of cylinder lid 1116: 76.05 mm (±0.05 mm)
Inner diameter x of cylinder lid 1116: 70.5 mm (±0.05 mm)
Thickness y of cylinder lid 1116 including lip 1154: 12.7 mm
Thickness z of cylinder lid 1116 without lip 1154: 6.35 mm
Diameter a of first lid opening 1134: 22.25 mm (±0.02 mm)
Diameter b of second lid opening 1136: 12.7 mm (±0.1 mm)
Distance between centers of first and second lid openings 1134 and 1136: 23.5 mm
The weight 1112 specification details are:
Outer diameter c: 50.0 mm
Diameter d of center bore 1130: 16.0 mm
Height e: 39.0 mm
The piston head 1118 specification details are:
Diameter f: 59.7 mm (±0.05 mm)
Height g: 16.5 mm. Piston head height must not be less than 15.0 mm.

Outer holes 1214 (14 total) with a 9.30 (±0.25) mm diameter h, outer holes 1214 equally spaced with centers being 23.9 mm from the center of center hole 1218.
Inner holes 1216 (7 total) with a 9.30 (±0.25) mm diameter i, inner holes 1216 equally spaced with centers being 13.4 mm from the center of center hole 1218.
Center hole 1218 has a diameter j of approximately ⅝ inches (15.9 mm) and is threaded to accept a lower portion 1146 of piston shaft 1114.

Prior to use, the stainless steel screens (not shown) of the piston head 1118 and cylinder 1120 should be inspected for clogging, holes or over-stretching and replaced when necessary. A urine permeability measurement apparatus with damaged screen can deliver erroneous UPM results, and must not be used until the screen has been replaced.

A 5.00 cm mark 1156 is scribed on the cylinder 1120 at a height k of 5.00 cm (±0.05 cm) above the screen (not shown) attached to the bottom 1148 of the cylinder 1120. This marks the fluid level to be maintained during the analysis. Maintenance of correct and constant fluid level (hydrostatic pressure) is critical for measurement accuracy.

A constant hydrostatic head reservoir 1014 is used to deliver salt solution 1032 to the cylinder 1120 and to maintain the level of salt solution 1032 at a height k of 5.00 cm above the screen (not shown) attached to the bottom 1148 of the cylinder 1120. The bottom 1034 of the air-intake tube 1010 is positioned so as to maintain the salt solution 1032 level in the cylinder 1120 at the required 5.00 cm height k during the measurement, i.e., bottom 1034 of the air tube 1010 is in approximately same plane 1038 as the 5.00 cm mark 1156 on the cylinder 1120 as it sits on the cover plate 1047 and supporting ring 1040 (with circular inner opening of not less than 64 mm diameter) above the receiving vessel 1024.

The cover plate 1047 and supporting ring 1040 are parts as used in the equipment used for the method "K(t) Test Method (Dynamic Effective Permeability and Uptake Kinetics Measurement Test method)" as described in EP 2 535 027 A1 and is called "Zeitabhängiger Durchlässigkeitsprüfstand" or "Time Dependent Permeability Tester", Equipment No. 03-080578 and is commercially available at BRAUN GmbH, Frankfurter Str. 145, 61476 Kronberg, Germany. Upon request, detailed technical drawings are also available.

Proper height alignment of the air-intake tube 1010 and the 5.00 cm mark 1156 on the cylinder 1120 is critical to the analysis. A suitable reservoir 1014 consists of a jar 1030 containing: a horizontally oriented L-shaped delivery tube 1018 connected to a flexible tube 1045 (e.g. Tygon tube, capable to connect nozzle and reservoir outlet) and to a Tygon tube nozzle 1044 (inner diameter at least 6.0 mm, length appr. 5.0 cm) for fluid delivery, a vertically oriented open-ended tube 1010 for admitting air at a fixed height within the constant hydrostatic head reservoir 1014, and a stoppered vent 1012 for re-filling the constant hydrostatic head reservoir 1014. Tube 1010 has an internal diameter of approximately 12 mm, but not less than 10.5 mm. The delivery tube 1018, positioned near the bottom 1042 of the constant hydrostatic head reservoir 1014, contains a stopcock 1020 for starting/stopping the delivery of salt solution 1032. The outlet 1044 of the delivery flexible tube 1045 is dimensioned (e.g. outer diameter 10 mm) to be inserted through the second lid opening 1136 in the cylinder lid 1116, with its end positioned below the surface of the salt solution 1032 in the cylinder 1120 (after the 5.00 cm height of the salt solution 1032 is attained in the cylinder 1120). The air-intake tube 1010 is held in place with an o-ring collar 1049. The constant hydrostatic head reservoir 1014 can be positioned on a laboratory reck 1016 at a suitable height relative to that of the cylinder 1120. The components of the constant hydrostatic head reservoir 1014 are sized so as to rapidly fill the cylinder 1120 to the required height (i.e., hydrostatic head) and maintain this height for the duration of the measurement. The constant hydrostatic head reservoir 1014 must be capable of delivering salt solution 1032 at a flow rate of at least 2.6 g/sec for at least 10 minutes.

The piston/cylinder assembly 1028 is positioned on the supporting ring 1040 in the cover plate 1047 or suitable alternative rigid stand. The salt solution 1032 passing through the piston/cylinder assembly 1028 containing the swollen hydrogel layer 1318 is collected in a receiving vessel 1024, positioned below (but not in contact with) the piston/cylinder assembly 1028.

The receiving vessel 1024 is positioned on the balance 1026 which is accurate to at least 0.001 g. The digital output of the balance 1026 is connected to a computerized data acquisition system 1048.

Figure 10:
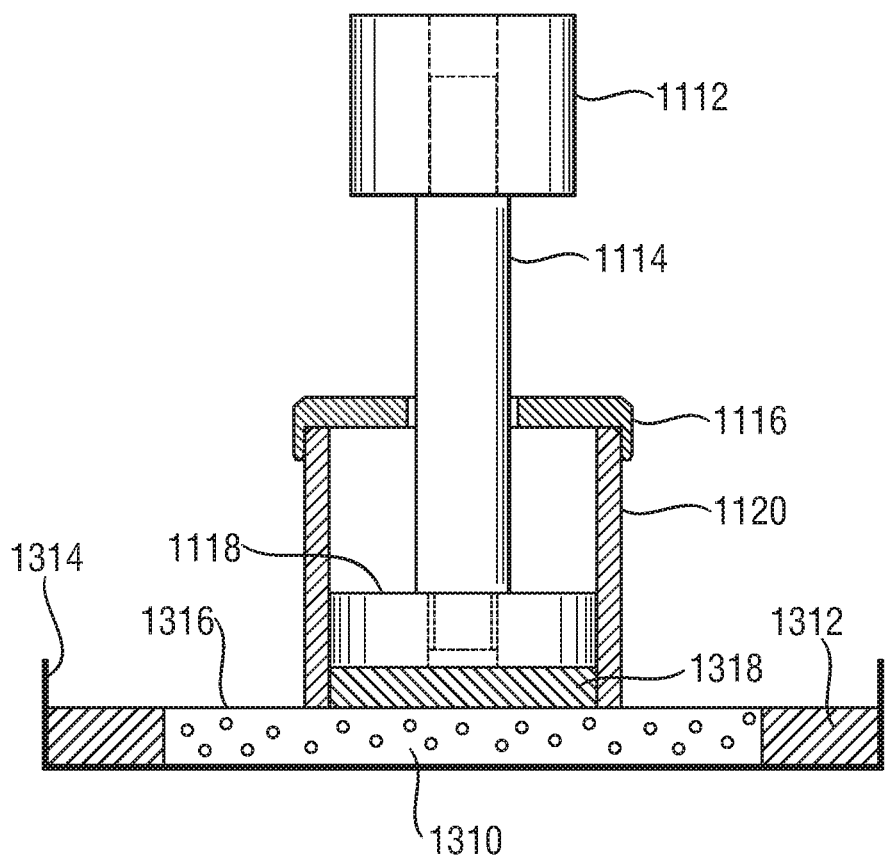
FIG. 10 is a cross-sectional side view of the piston/cylinder assembly of FIG. 8 placed on fritted disc for the swelling phase.

Preparation of Reagents (not illustrated) Jayco Synthetic Urine (JSU) 1312 (see FIG. 10) is used for a swelling phase (see UPM Procedure below) and 0.118 M Sodium Chloride (NaCl) Solution 1032 is used for a flow phase (see UPM Procedure below). The following preparations are referred to a standard 1 liter volume. For preparation of volumes other than 1 liter, all quantities are scaled accordingly.

JSU: A 1 L volumetric flask is filled with distilled water to 80% of its volume, and a magnetic stir bar is placed in the flask. Separately, using a weighing paper or beaker the following amounts of dry ingredients are weighed to within ±0.01 g using an analytical balance and are added quantitatively to the volumetric flask in the same order as listed below. The solution is stirred on a suitable stir plate until all the solids are dissolved, the stir bar is removed, and the solution diluted to 1 L volume with distilled water. A stir bar is again inserted, and the solution stirred on a stirring plate for a few minutes more.

Quantities of salts to make 1 liter of Jayco Synthetic Urine:
Potassium Chloride (KCl) 2.00 g
Sodium Sulfate (Na2SO4) 2.00 g
Ammonium dihydrogen phosphate (NH4H2PO4) 0.85 g
Ammonium phosphate, dibasic ((NH4)2HPO4) 0.15 g
Calcium chloride (CaCl2) 0.19 g—[or hydrated calcium chloride (CaCl2.2H2O) 0.25 g]
Magnesium chloride (MgCl2) 0.23 g—[or hydrated magnesium chloride (MgCl2.6H2O) 0.50 g]

To make the preparation faster, potassium chloride, sodium sulfate, ammonium dihydrogen phosphate, ammonium phosphate (dibasic) and magnesium chloride (or hydrated magnesium chloride) are combined and dissolved in the 80% of distilled water in the 1 L volumetric flask. Calcium chloride (or hydrated calcium chloride) is dissolved separately in approximately 50 ml distilled water (e.g. in a glass beaker) and the calcium chloride solution is transferred to the 1 L volumetric flask after the other salts are completely dissolved therein. Afterwards, distilled water is added to 1 L (1000 ml 0.4 ml) and the solution is stirred for a few minutes more. Jayco synthetic urine may be stored in a clean plastic container for 10 days. The solution should not be used if it becomes cloudy.

0.118 M Sodium Chloride (NaCl) Solution: 0.118 M Sodium Chloride is used as salt solution 1032. Using a weighing paper or beaker 6.90 g (±0.01 g) of sodium chloride is weighed and quantitatively transferred into a 1 L volumetric flask (1000 ml±0.4 ml); and the flask is filled to volume with distilled water. A stir bar is added and the solution is mixed on a stirring plate until all the solids are dissolved.

The conductivity of the prepared Jayco solution must be in the range of appr. 7.48-7.72 mS/cm and of the prepared 0.118 M Sodium Chloride (NaCl) Solution in the range of appr. 12.34-12.66 mS/cm (e.g. measured via COND 70 INSTRUMENT without CELL, #50010522, equipped with Cell VPT51-01 C=0.1 from xs instruments or via LF 320/ Set, #300243 equipped with TetraCon 325 from WTW or COND 330i, #02420059 equipped with TetraCon 325 from WTW). The surface tension of each of the solutions must be in the range of 71-75 mN/m (e.g. measured via tensiometer K100 from Kruess with Pt plate).

Test Preparation

Using a solid reference cylinder weight (not shown) (50 mm diameter; 128 mm height), a caliper gauge (not shown) (measurement range 25 mm, accurate to 0.01 mm, piston pressure max. 50 g; e.g. Mitutoyo Digimatic Height Gage) is set to read zero. This operation is conveniently performed on a smooth and level bench (not shown) of at least approximately 11.5 cm×15 cm. The piston/cylinder assembly 1028 without superabsorbent polymer particles is positioned under the caliper gauge (not shown) and a reading, L1, is recorded to the nearest 0.01 mm.

The constant hydrostatic head reservoir 1014 is filled with salt solution 1032. The bottom 1034 of the air-intake tube 1010 is positioned so as to maintain the top part (not shown) of the liquid meniscus (not shown) in the cylinder 1120 at the 5.00 cm mark 1156 during the measurement. Proper height alignment of the air-intake tube 1010 at the 5.00 cm mark 1156 on the cylinder 1120 is critical to the analysis.

The receiving vessel 1024 is placed on the balance 1026 and the digital output of the balance 1026 is connected to a computerized data acquisition system 1048. The cover plate 1047 with the supporting ring 1040 is positioned above the receiving vessel 1024.

UPM Procedure 1.5 g (±0.05 g) of superabsorbent polymer particles is weighed onto a suitable weighing paper or weighing aid using an analytical balance. The moisture content of the superabsorbent polymer particles is measured according to the Edana Moisture Content Test Method NWSP 230.0.R2 (15) or via a Moisture Analyzer (HX204 from Mettler Toledo, drying temperature 130° C., starting superabsorber weight 3.0 g (±0.5 g), stop criterion 1 mg/140 s). If the moisture content of the superabsorbent polymer particles is greater than 3 wt %, then the superabsorbent polymer particles are dried to a moisture level of <3 wt %, e.g. in an oven at 105° C. for 3 h or e.g. at 120° C. for 2 h. Agglomerated superabsorbent polymer particles are dried if moisture level is greater than 5 wt %, e.g. in an oven at 105° C. for 3 h or e.g. at 120° C. for 2 h.

The empty cylinder 1120 is placed on a level benchtop 1046 (not shown) and the superabsorbent polymer particles are quantitatively transferred into the cylinder 1120. The superabsorbent polymer particles are evenly dispersed on the screen (not shown) attached to the bottom 1148 of the cylinder 1120 while rotating the cylinder 1120, e.g. aided by a (manual or electrical) turn table (e.g. petriturn-E or petriturn-M from Schuett). It is important to have an even distribution of particles on the screen (not shown) attached to the bottom 1148 of the cylinder 1120 to obtain the highest precision result. After the superabsorbent polymer particles have been evenly distributed on the screen (not shown) attached to the bottom 1148 of the cylinder 1120 particles must not adhere to the inner cylinder walls 1150. The piston shaft 1114 is inserted through the first lid opening 1134, with the lip 1154 of the lid 1116 facing towards the piston head 1118. The piston head 1118 is carefully inserted into the cylinder 1120 to a depth of a few centimeters. The lid 1116 is then placed onto the upper rim 1144 of the cylinder 1120 while taking care to keep the piston head 1118 away from the superabsorbent polymer particles. The weight 1112 is positioned on the upper portion 1128 of the piston shaft 1114 so that it rests on the shoulder 1124 such that the first and second linear index marks are aligned. The lid 1116 and piston shaft 1126 are then carefully rotated so as to align the third, fourth, fifth, and sixth linear index marks are then aligned with the first and the second linear index marks. The piston head 1118 (via the piston shaft 1114) is then gently lowered to rest on the dry superabsorbent polymer particles. Proper seating of the lid 1116 prevents binding and assures an even distribution of the weight on the hydrogel layer 1318.

Swelling Phase:

A fritted disc of at least 8 cm diameter (e.g. 8-9 cm diameter) and at least 5.0 mm thickness (e.g. 5-7 mm thickness) with porosity "coarse" or "extra coarse" (e.g. Chemglass Inc. #CG 201-51, coarse porosity; or e.g. Robu 1680 with porosity 0) 1310 is placed in a wide flat-bottomed Petri dish 1314 and JSU 1312 is added by pouring JSU 1312 onto the center of the fritted disc 1310 until JSU 1312 reaches the top surface 1316 of the fritted disc 1310. The JSU height must not exceed the height of the fritted disc 1310. It is important to avoid any air or gas bubbles entrapped in or underneath the fritted disc 1310.

The entire piston/cylinder assembly 1028 is lifted and placed on the fritted disc 1310 in the Petri dish 1314. JSU 1312 from the Petri dish 1314 passes through the fritted disc 1310 and is absorbed by the superabsorbent polymer particles (not shown) to form a hydrogel layer 1318. The JSU 1312 available in the Petri dish 1314 should be enough for all the swelling phase. If needed, more JSU 1312 may be added to the Petri dish 1314 during the hydration period to keep the JSU 1312 level at the top surface 1316 of the fritted disc 1310. After a period of 60 minutes, the piston/cylinder assembly 1028 is removed from the fritted disc 1310, taking care to ensure the hydrogel layer 1318 does not lose JSU 1312 or take in air during this procedure. The piston/cylinder assembly 1028 is placed under the caliper gauge (not shown) and a reading, L2, is recorded to the nearest 0.01 mm. If the reading changes with time, only the initial value is recorded. The thickness of the hydrogel layer 1318, L0 is determined from L2−L1 to the nearest 0.1 mm.

The piston/cylinder assembly 1028 is transferred to the supporting ring 1040 in the cover plate 1047. The constant hydrostatic head reservoir 1014 is positioned such that the delivery tube nozzle 1044 is placed through the second lid opening 1136. The measurement is initiated in the following sequence:

a) The stopcock 1020 of the constant hydrostatic head reservoir 1014 is opened to permit the salt solution 1032 to reach the 5.00 cm mark 1156 on the cylinder 1120. This salt solution 1032 level should be obtained within 10 seconds of opening the stopcock 1020.

b) Once 5.00 cm of salt solution 1032 is attained, the data collection program is initiated.

With the aid of a computer 1048 attached to the balance 1026, the quantity g (in g to accuracy of 0.001 g) of salt solution 1032 passing through the hydrogel layer 1318 is recorded at intervals of 20 seconds for a time period of 10 minutes. At the end of 10 minutes, the stopcock 1020 on the constant hydrostatic head reservoir 1014 is closed.

The data from 60 seconds to the end of the experiment are used in the UPM calculation. The data collected prior to 60 seconds are not included in the calculation.

For each time period of 20 seconds (time $t_{(i-1)}$ to $t_i$) after the initial 60 seconds of the experiment, the respective flow rate $F_{S_{(i)}}$ (in g/s) and the respective mid-point of the time $t_{(1/2)_t}$ (in s) is calculated according to the following formulas:

$$Fs_{(t)} = \frac{(g_{(i-1)} - g_{(i)})}{(t_{(i-1)} - t_{(i)})} \text{ and } t_{(1/2)_t} = \frac{(t_{(i-1)} + t_{(i)})}{2} \quad (I)$$

The flow rate $F_{S_{(t)}}$ of each time interval ($t_{(i-1)}$ to $t_i$) is plotted versus the mid-point of the time $t_{(1/2)_t}$ of the time interval ($t_{(i-1)}$ to $t_i$). The intercept is calculated as Fs(t=0).

Calculation of the Intercept:

The intercept is calculated via a best-fit regression line, e.g. as following: the equation for the intercept of the regression line, a, is:

$$a = y_{AVG} - b \cdot s_{AVG} \quad (II)$$

where the slope, b, is calculated as:

$$b = \frac{\sum (x - x_{AVG}) \cdot (y - y_{AVG})}{\sum (x - x_{AVG})^2} \quad (III)$$

and where $x_{AVG}$ and $y_{AVG}$ are the sample means AVERAGE of the known x's and AVERAGE of the known_y's, respectively.

Calculation of Urine Permeability Measurement Q:

The intercept Fs(t=0) is used to calculate Q according to the following formula:

$$Q = \frac{F_s(t=0) \cdot L_0}{\rho \cdot A \cdot \Delta P} \quad (IV)$$

where the flow rate Fs(t=0) is given in g/s, $L_0$ is the initial thickness of the hydrogel layer 1318 in cm, ρ is the density of the salt solution 1032 in $g/cm^3$ (e.g. 1.003 $g/cm^3$ at room temperature). A (from the equation above) is the area of the hydrogel layer 1318 in $cm^2$ (e.g. 28.27 $cm^2$), ΔP is the hydrostatic pressure in $dyne/cm^2$ (e.g. 4920 $dyne/cm^2$), and the Urine Permeability Measurement, Q, is in units of $cm^3$ sec/g. The average of three determinations should be reported.

TABLE 1

| Variable | Description | Unit |
|---|---|---|
| $g_i$ | Mass of salt solution 1032 flown through the swollen gel layer (recorded by the balance) at the time $t_i$ (accuracy 0.001 g) | g |
| $t_i$ | Time point (every 20 s) | s |
| $t_{(1/2)_t}$ | Mid-point of time for the respective time interval $t_{i-1}$ to $t_i$ | s |
| $Fs_t$ | Flow Rate at the time interval $t_{i-1}$ to $t_i$ | g/s |
| Fs (t = 0) | Intercept flow rate at t = 0 s from the plot of the flow rate Fs(t) vs. the mid-point of time $t_{(1/2)_t}$. | g/s |
| $L_0$ | Thickness of the swollen gel layer (swollen with JSU 1312) before the salt solution 1032 flows through the gel layer. | cm |
| ρ | Density of the salt solution 1032 (1.003 $g/cm^3$) | $g/cm^3$ |
| A | Area of the swollen gel layer (28.27 $cm^2$) | $cm^2$ |

TABLE 1-continued

| Variable | Description | Unit |
|---|---|---|
| ΔP | Hydrostatic pressure across the gel layer (4920 dyne/cm$^2$) | dyne/cm$^2$ |
| Q | Urine Permeability Measurement | cm$^3$ * sec/g |

Staining of surface-coated water-absorbing polymer particles with 20 ppm Toluidine Blue O in 0.9% wt and 10% wt NaCl solution test method 1. Solution Preparation:

Saline Preparation:

Using a weighing paper or beaker the respective amount of sodium chloride (±0.01 g) is weighed and quantitatively transferred into a 1 L volumetric flask (1000 ml±0.4 ml); and the flask is filled to volume with deionized water. A stir bar is added and the solution is mixed on a stirring plate until all the solids are dissolved.

Amount of Sodium Chloride:

For 0.9% wt Saline: 9.00 g NaCl

For 10% wt Saline: 100.00 g NaCl

For 15% wt Saline: 150.00 g NaCl

The surface tension of each of the solutions should be in the range of 71-75 mN/m (e.g. measured via tensiometer K100 from Kruess with Pt plate).

First Solution in 0.9% Wt Saline:

20 mg Toluidine Blue O (CAS: 540-23-8) are dissolved in 250 ml 0.9% wt NaCl solution. The mixture is placed into an ultrasonic bath for 1 hour, filtered through a paper filter (e.g. of the type Whatman 589/1, ashless/Black ribbon), and filled up to 1000 (±5) ml with 0.9% wt NaCl solution.

Second Solution in 10% Wt Saline:

20 mg Toluidine Blue O (CAS: 540-23-8) are dissolved in 250 ml 10% wt NaCl solution. The mixture is placed into an ultrasonic bath for 1 hour, filtered through a paper filter (e.g. of the type Whatman 589/1, ashless/Black ribbon), and filled up to 1000 (±5) ml with 10% wt NaCl solution.

2. Staining Procedure:

A sample of 30-50 mg of dry superabsorbent polymer particles is placed into each of two 40 ml screw cap glass vials (i.e. 30-50 mg superabsorbent particles in each vial), and 30 ml of the first staining solution is added to the first vial and 30 ml of the second solution is added to the second vial. The vials are closed, and the superabsorbent polymer particles are allowed to swell and equilibrate for 18 hours at 20-25° C. during (optional) gentle agitation (e.g. gentle swirling or slow rolling of the vial on a roller mill).

For microscopy assessment, the swollen, stained samples of superabsorbent polymer particles are transferred into transparent glass dishes or watch glasses, and covered with the respective pure saline (no toluidine blue containing) solution. Alternatively, they can be placed into 1 cm glass or quartz cuvettes with a stopper in contact with the added respective saline solution.

A stereomiscroscope (e.g. Keyence Multi View System VHX-S550E, equipped with a transmittance setup and objective like Keyence Standard Zoomobjectiv VHX-Z20T (magnification 20-200×)) in transmission mode may be used for evaluation of the swollen, stained superabsorbent polymer particles.

Figure 11:
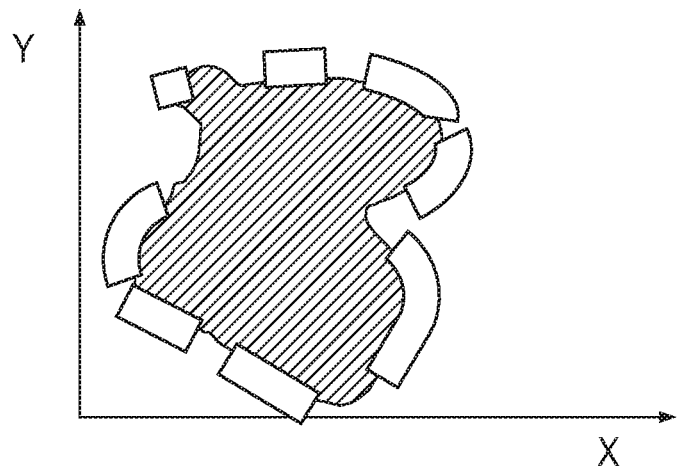
FIG. 11 is a schematic view of surface-coated water-absorbing polymer particles having a ruptured coating layer.

3. Evaluation of the Caliper of Outer Shell (i.e. Coating Layer):

The swollen particles from both the 0.9% wt and the 10% wt saline solutions are visualized in transmission mode on the microscope. A distinct continuous layer on the periphery of the particles is sought to be established wherein the coloration level of shell and core areas of the particles are visibly different and said areas are distinguishable. When the shell area is identified and more than 5 separate discontinuities in such a layer are identified per particle or if less than about 75% of the visual perimeter of the particle has a shell present, this is regarded to as a ruptured shell particle (FIG. 11). Rupture may occur more easily in the first solution wherein the osmotic pressure of swelling is larger and may lead to higher level of shell stretching. If the particles from the first solution are ruptured more than 75% in number (when at least 20 particles are taken as sample), the evaluation of shell caliper is done on the particles swollen in the second (10% wt saline) solution. The higher concentration of NaCl in the second solution is to prevent overstretching of shell area of particles. In case that over 75% in number of particles have ruptured shells in the second solution, the measurement is repeated with a third solution of 15% wt NaCl. For caliper and caliper ratio measurements it is necessary to select at least 10 particles with non-ruptured shells (FIG. 12).

Figure 12:
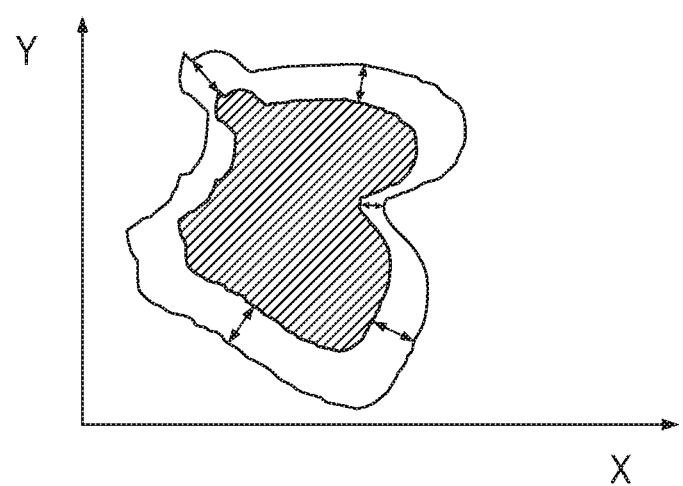
FIG. 12 is a schematic view of surface-coated water-absorbing polymer particles having a continuous coating layer and examples of $C_i$ measurements according to the staining of surface-coated water-absorbing polymer particles with 20 ppm Toluidine Blue O in 0.9% wt and 10% wt NaCl solution test method.

For both solutions, once a non-ruptured layer of shell area is established on the image, according to the description above, the caliper is measured as the shortest distance from the surface of the particle (outer border) to the inner border of the shell, i.e. the transition line between the areas of different coloration level, as shown on FIG. 12. At least five different measurements of caliper shall be taken (i.e. i≥5) per particle, which individual measurements should be relatively uniformly distributed along the visual perimeter of the particle, i.e. the relative distance between individual measurements along the perimeter of the particle should be about 15-30% of the whole perimeter. The five data points ($C_i$, i≥5) for each selected particle j of the set of at least ten particles (j≥10), are recorded.

4. Evaluation of Thinnest-to-Thickest Caliper Ratio:

From the 5 measurements for each measured particle, the maximum and the minimum values for the caliper are taken and the respective ratio is calculated for each particle ($R_j$) according to Formula (V). Finally, the arithmetic average of the single particle maximum to minimum caliper ratios $R_j$ over the 10 particles is calculated, according to Formula (VI). The average max/min caliper ratios $R_{avg}$ are recorded for both solutions, or at least for the second solution in case of rupture of over 75% of the particles in the first solution. If rupture >75% in number of particles with the second solution, the test method is repeated with a third solution, i.e. 20 ppm toluidine blue solution in 15% wt saline and 15% wt saline solution.

$$R_j = \frac{\max_i C_i}{\min_i C_i} \qquad (V)$$

$$R_{avg} = \frac{1}{n}\sum_{i}^{j=n} R_j \qquad (VI)$$

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for making surface-coated water-absorbing polymer particles in a microfluidic device, wherein the microfluidic device comprises:
   a first microfluidic channel conveying precursor water-absorbing polymer particles,
   a second microfluidic channel conveying a first coating solution,
   a third microfluidic channel conveying precursor water-absorbing polymer particles coated with the first coating solution,
   a fourth microfluidic channel conveying a first non aqueous liquid selected from hydrocarbon oil, liquid fatty alcohol, fluorinated oil and silicone oil,
   a first intersection between the first microfluidic channel and the second microfluidic channel, and
   a second intersection between the third microfluidic channel and the fourth microfluidic channel, wherein the third microfluidic channel is in communication with the first intersection and the second intersection,
   the method comprising the steps of:
   a) providing precursor water-absorbing polymer particles, the first coating solution and the first non aqueous liquid,
   b) feeding the precursor water-absorbing polymer particles in the first microfluidic channel of the microfluidic device,
   c) feeding the first coating solution in the second microfluidic channel of the microfluidic device,
   d) feeding the first non aqueous liquid in the fourth microfluidic channel of the microfluidic device,
   e) coating precursor water-absorbing polymer particles with the first coating solution at the first intersection and/or in the third microfluidic channel,
   f) conveying the precursor water-absorbing polymer particles coated with the first coating solution through the third microfluidic channel toward the second intersection,
   g) separating the precursor water-absorbing polymer particles coated with the first coating solution from each other with the first non aqueous liquid at the second intersection, and
   h) polymerizing or crosslinking the first coating on the coated water-absorbing polymer particles to obtain surface-coated water-absorbing polymer particles;
   wherein in step (b) the polymer particles travel from the first microfluidic channel to the first intersection under pulsating flow;
   wherein in step (e) the first coating solution contacts the polymer particles under laminar flow conditions; and
   wherein in step (g) said first coating solution has a flow that is laminar.

2. The method according to claim 1 wherein a further step comprises collecting surface-coated water-absorbing polymer particles in a vessel after step h).

3. The method according to claim 1 including further steps which comprise i) conveying the surface-coated water-absorbing polymer particles through a fifth microfluidic channel toward a third intersection and j) coating the surface-coated water-absorbing polymer particles with the first coating solution or with a second coating solution at the third intersection and/or in a sixth microfluidic channel, wherein the second coating solution is different from the first coating solution.

4. The method according to claim 1 wherein the precursor water-absorbing polymer particles coated with the first coating solution are obtained in the microfluidic device by the techniques selected from the group consisting of hydrodynamic flow focusing, coaxial shear flow, crossflow shear in cross junction, coflow junction and T-junction microchannel geometries.

5. The method according to claim 1 wherein the precursor water-absorbing polymer particles are dispersed in a carrier liquid, wherein the carrier liquid is the first non aqueous liquid or a second non aqueous liquid selected from hydrocarbon oil, liquid fatty alcohol, fluorinated oil and silicone oil, and the second non aqueous liquid is different from the first non aqueous liquid.

6. The method according to claim 1 wherein the precursor water-absorbing polymer particles comprise crosslinked polymers of polyacrylic acids or their salts or polyacrylates or derivatives thereof.

7. The method according to claim 1 wherein the precursor water-absorbing polymer particles have, prior to coating, an absorption capacity of at least 20 g/g according to the CRC test method.

8. The method according to claim 1 wherein the first coating solution comprises particles such as inorganic solids particles, and either polymerizable monomers and/or oligomers, or crosslinkable polymers.

9. The method according to claim 8 wherein the inorganic solids particles are clay platelets.

10. The method according to claim 1 wherein the first coating solution comprises a polymerization initiator system and wherein in step h), the polymerization is initiated by activation of the polymerization initiator system by applying heat and/or radiation onto the microfluidic device.

11. The method according to claim 1 wherein the coating layer on the surface-coated water-absorbing polymer particles in dry state has an average caliper from 1 to 100 µm.

12. The method according to claim 1 wherein the high sorption capacity of the surface-coated water-absorbing polymer particles is at least 10 g/g according to the CRC test method.

* * * * *